United States Patent
Cheng et al.

(10) Patent No.: US 11,472,815 B2
(45) Date of Patent: Oct. 18, 2022

(54) 1,4-DIPHENYL-1H-IMIDAZOLE AND 2,4-DIPHENYLTHIAZOLE DERIVATIVES AND PREPARATION METHOD THEREFOR AND USE THEREOF

(71) Applicant: SOUTHERN MEDICAL UNIVERSITY, Guangzhou (CN)

(72) Inventors: Kui Cheng, Guangzhou (CN); Shuwen Liu, Guangzhou (CN); Gengzhen Zhu, Guangzhou (CN)

(73) Assignee: SOUTHERN MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 17/043,646

(22) PCT Filed: Apr. 9, 2018

(86) PCT No.: PCT/CN2018/082243
§ 371 (c)(1),
(2) Date: Sep. 29, 2020

(87) PCT Pub. No.: WO2019/195972
PCT Pub. Date: Oct. 17, 2019

(65) Prior Publication Data
US 2021/0017189 A1    Jan. 21, 2021

(51) Int. Cl.
C07D 495/04 (2006.01)
C07D 233/64 (2006.01)
C07D 277/28 (2006.01)

(52) U.S. Cl.
CPC ......... *C07D 495/04* (2013.01); *C07D 233/64* (2013.01); *C07D 277/28* (2013.01)

(58) Field of Classification Search
CPC ... C07D 495/04; C07D 233/64; C07D 277/28
See application file for complete search history.

(56) References Cited

FOREIGN PATENT DOCUMENTS

WO    2015171951 A1    11/2015

OTHER PUBLICATIONS

Eeda Venkateswararao et al., Exploration and Optimization of an Efficient One-pot Sequential Synthesis of Di/tri-substituted Thiazoles from α-Bromoketones, Thioacids Salt, and Ammonium Acetate, Journal of Heterocyclic Chemistry, 2015, pp. 1449-1456.
Norihiro Ikemoto et al., Practical routes to the triarylsulfonyl chloride intermediate of a b3 adrenergic receptor agonist, Tetrahedron, 2003, pp. 1317-1325, vol. 59.
Ruslan Medzhitov et al. A human homologue of the *Drosophila* Toll protein signals activation of adaptive immunity, Nature, 1997, pp. 394-397, vol. 388.

*Primary Examiner* — Rebecca L Anderson
(74) *Attorney, Agent, or Firm* — Bayramoglu Law Offices LLC

(57) ABSTRACT

Provided are 1,4-diphenyl-1H-imidazole and 2,4-diphenylthiazole derivatives having a structure represented by Formula I, a preparation method therefor and uses thereof:

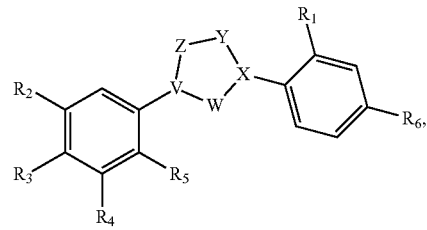

Formula I wherein $R_1$ is any one of H, OH, and $OCH_3$, $R_2$ is any one of H, $NO_2$, $CH_3$, $CF_3$, $SO_2CH_3$, $COOCH_3$, or $CONHCH_3$, $R_3$ is any one of H, $NO_2$, $OCH_3$, or $CF_3$, $R_4$ is selected from H, $CF_3$, or Cl, $R_5$ is any one of H, Cl, $CF_3$, or $NHCH_3$, and $R_6$ is any one of $OCF_3$, $CF_3$, or CN; V is either C or N, W is either CH or N, X is a C atom, Y is either CH or N, and Z is either CH or S. This compound can be used in preparation of anti-inflammatory adjuvants, TLR1 or TLR2 agonists, and anti-tumor agents and for regulating the activity activation level of TLR1 and TLR2 alkaline phosphatases in vitro and in vivo.

4 Claims, 3 Drawing Sheets

1,4-DIPHENYL-1H-IMIDAZOLE AND 2,4-DIPHENYLTHIAZOLE DERIVATIVES AND PREPARATION METHOD THEREFOR AND USE THEREOF

CROSS REFERENCE TO THE RELATED APPLICATIONS

This application is the national phase entry of International Application No. PCT/CN2018/082243, filed on Apr. 9, 2018, the entire contents of which are incorporated herein by reference.

TECHNICAL FIELD

The present invention relates to the fields of medicine and health and chemical engineering, and specifically to a series of compounds of TLR1/2 agonists, which can be used in the fields of scientific research, health care and chemical engineering.

BACKGROUND

The immune system is an important system for the body to implement immune responses and immune functions. It is composed of immune organs, immune cells and immune molecules. The function of the immune system is to recognize and eliminate antigenic foreign bodies to maintain a stable environment and physiological balance in the body. Autoimmune diseases are mainly caused by the accumulation of a large number of immune cells and immunoglobulins as a result of an excessive immune response.

The growth and development of mammals are accompanied by immune system disorders and inflammatory responses. The inflammatory response protects the body from harmful stimuli and invading pathogens by activating innate and adaptive immune responses to repair the immune system of damaged tissues. In this process, pattern recognition receptors are a type of recognition molecules that are mainly expressed on the surface of innate immune cells, are non-clonally distributed, and can recognize one or more pathogen-associated molecular patterns (PAMPs) or host-derived damage-associated molecular patterns (DAMPs), activate immune cells, and mediate innate immunity. They can be divided into four subfamilies: Toll-like receptors (TLRs), retinoic acid inducible gene I-like receptors (RLRs), NOD-like receptors (NLRs) and C-type lectin receptors (CLRs). Among them, Toll-like receptors are the most representative in identifying pathogenic microorganisms.

Since Medzhitov discovered Toll-like receptors in 1997, 13 members of the TLR family have been confirmed in mammals, and there are more than 10 functional member ligands for the TLRs in the human genome. Among them, TLR3 recognizes double-stranded RNA, TLR4 recognizes lipopolysaccharide, TLR5 recognizes bacterial flagellin, TLR7 and TLR8 recognize viral or bacterial single-stranded RNA, and TLR9 recognizes cytosine-phosphate-guanine (CpG). Meanwhile, TLR family members can dimerize with themselves or other TLRs to form homodimers or heterodimers such as TLR1/2 and TLR2/6, which, together with adaptor proteins, mediate downstream signal transduction. Currently, TLR modulators are available as agonists and inhibitors for the treatment of immune inflammation.

In the TLR family, TLR2 identifies the broadest spectrum of pathogens, including Gram-positive bacteria such as *Staphylococcus, Streptococcus pneumoniae, Mycoplasma*, yeast and *Escherichia coli*, and mainly mediates the signal transduction of the lipoprotein of Gram-positive bacteria infection to increase the expression of signal transduction molecules such as IL-1 and IL-12-related protein kinases, and tumor necrosis factor-related factors, and further promote the synthesis and release of effect factors such as IL-1 and 12 to initiate inflammation and induce the expression of genes for cell proliferation, transformation and apoptosis, thereby mediating the body's natural immune defense. The regulation of TLR1 and TLR2 activity is not only the goal of clinical treatment, but also a very meaningful scientific research subject.

SUMMARY

An objective of the present invention is to provide 1,4-diphenyl-1H-imidazole and 2,4-diphenylthiazole derivatives as represented by Formula I, which can activate TLR1/2 receptor activity to resist the occurrence and development of a series of tumors, such as breast cancer and bladder cancer, thereby providing a new approach for the treatment of these diseases. Therefore, these compounds are of important research and development value and development significance.

In an aspect, the present invention provides a compound, or a pharmaceutically acceptable salt thereof, wherein the compound has a structure represented by Formula I,

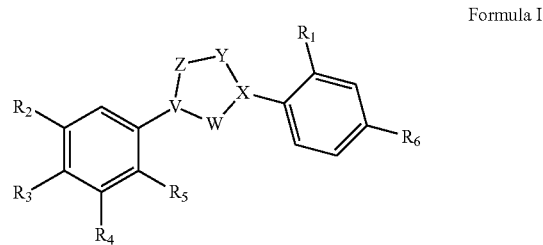

Formula I wherein $R_1$ is selected from the group consisting of H, OH, $OCH_3$, $OCH_2CH_3$, $OCH_2C_6H_5$, $O(CH_2)_2Br$, $O(CH_2)_3Br$, $O(CH_2)_2O(CH_2)_2Br$, $O(CH_2)_2O(CH_2)_2OH$, $OCOCH_3$, $OCO(CH_2)_2CH_3$, $OCO(CH_2)_{10}CH_3$, $OCOC_6H_5$, $OCOCH=CHC_6H_5$, $OSO_3H$, $O(CH_2)_2O(CH_2)_2O(CH_2)_2I$, $OCH_2CONH_2$, $O(CH_2)_2NH_2$, $O(CH_2)_2NH$-Biotin, $O(CH_2)_2O$-Biotin, or $O(CH_2)_2O(CH_2)_2O$-Biotin, $R_2$ is selected from the group consisting of H, $NO_2$, $CH_3$, $CF_3$, $SO_2CH_3$, $COOCH_3$, $CONHCH_3$, or $-N^+O-O^-$, $R_3$ is selected from the group consisting of H, $NO_2$, $OCH_3$, and $CF_3$, $R_4$ is selected from H, $CF_3$, or Cl, $R_5$ is selected from the group consisting of H, Cl, $CF_3$, or $NHCH_3$, and $R_6$ is selected from the group consisting of H, $OCF_3$, $CF_3$, or CN; V is either C or N, W is selected from either CH or N, X is C, Y is either CH or N, and Z is either CH or S.

In the technical solution of the present invention, the compound of Formula I is selected from a structure of Formula I-1 or I-2,

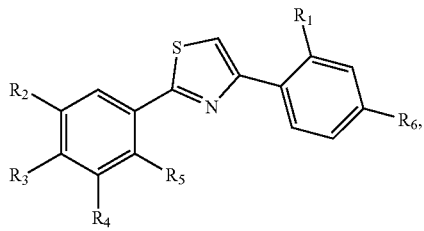

I-1

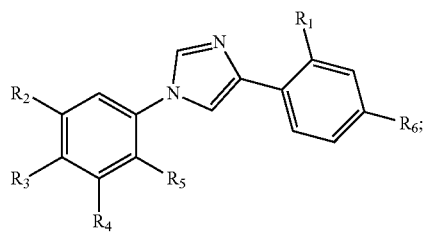

I-2 wherein the $R_1$-$R_6$ substituents are the same as above.

In the technical solution of the present invention, the compound has a structural formula below:

Compound 1

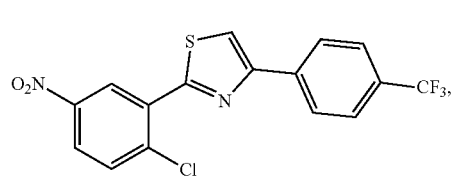

Compound 2

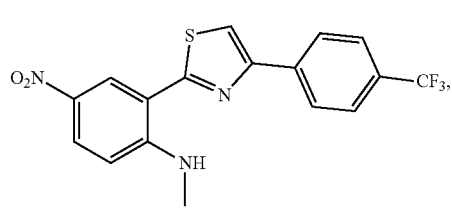

Compound 3

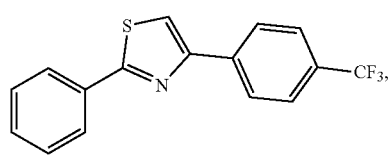

Compound 4

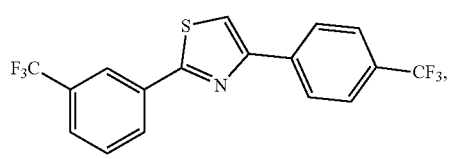

Compound 5

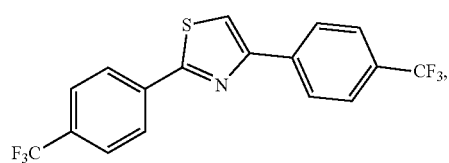

Compound 6

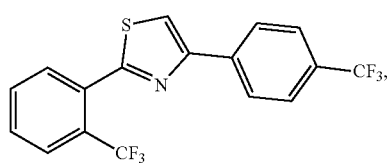

Compound 7

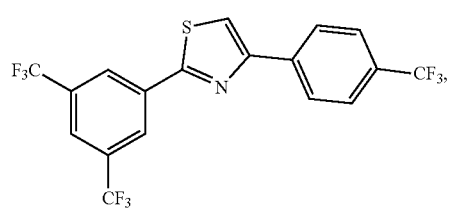

Compound 8

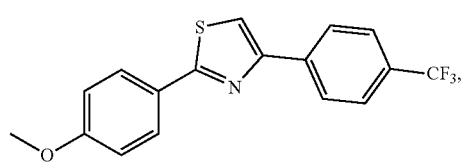

Compound 9

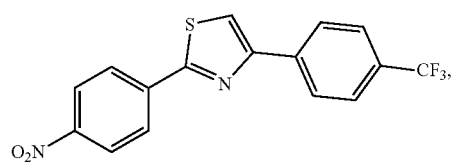

Compound 10

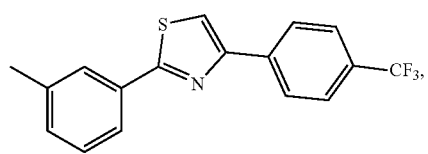

Compound 11

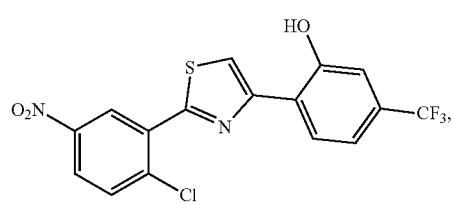

Compound 12

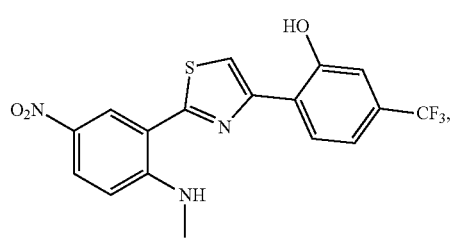

-continued
Compound 13
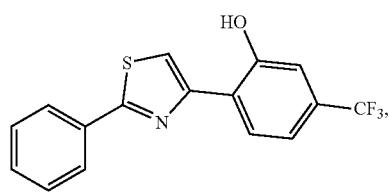
Compound 14
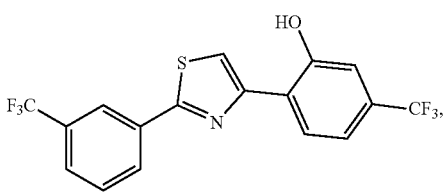
Compound 15
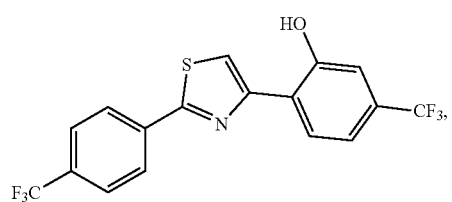
Compound 16
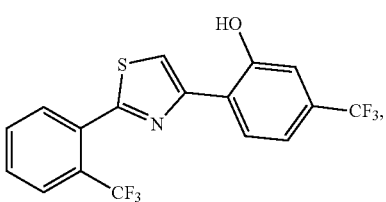
Compound 17
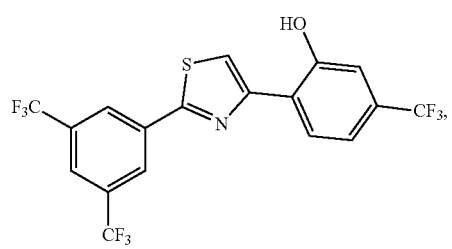
Compound 18
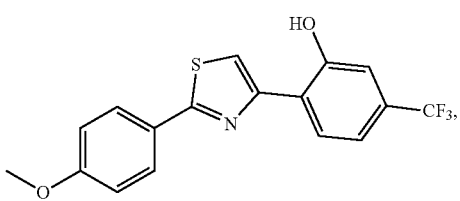
Compound 19
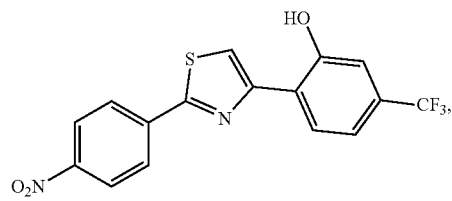
Compound 20
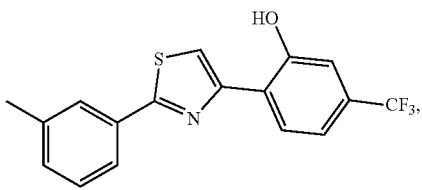
Compound 21
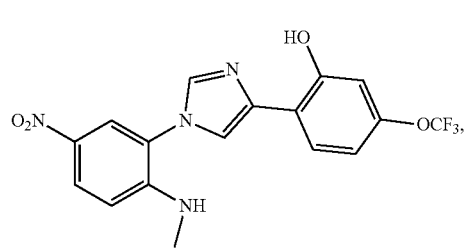
Compound 22
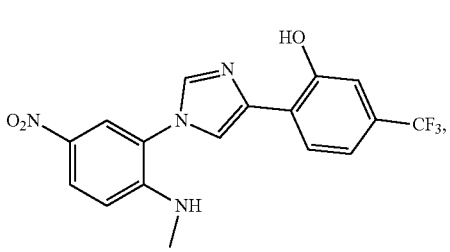
Compound 23
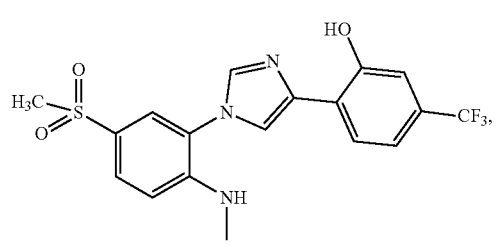
Compound 24
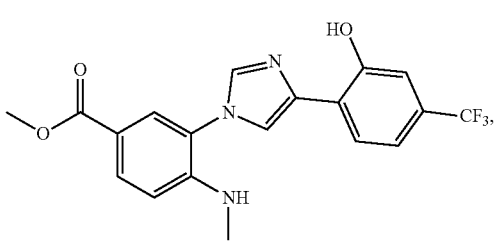
Compound 25
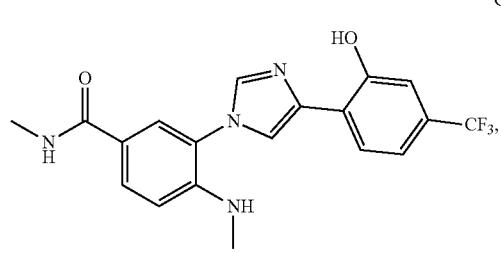
Compound 26
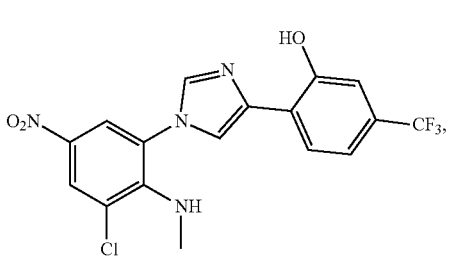

-continued
Compound 27
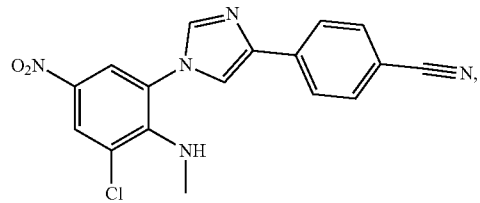
Compound 28
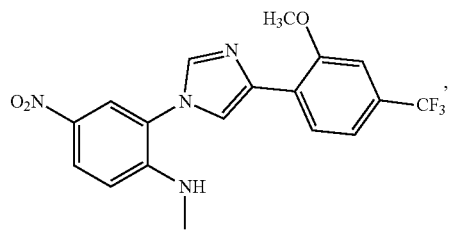
Compound 29
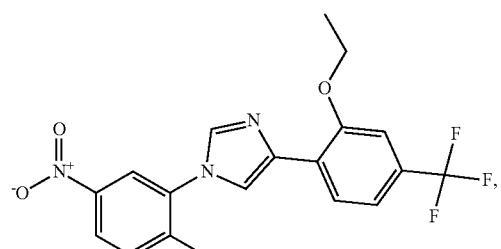
Compound 30
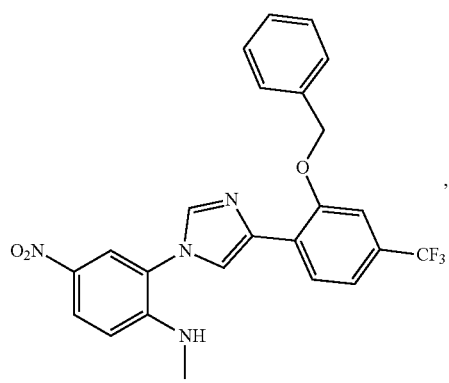
Compound 31
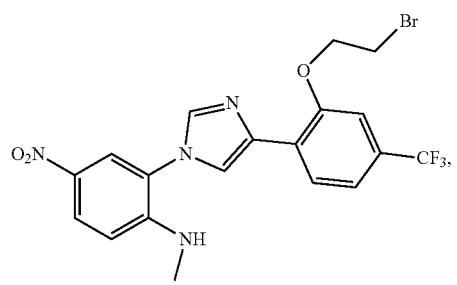
Compound 32
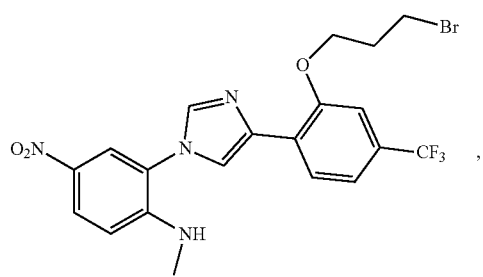
Compound 33
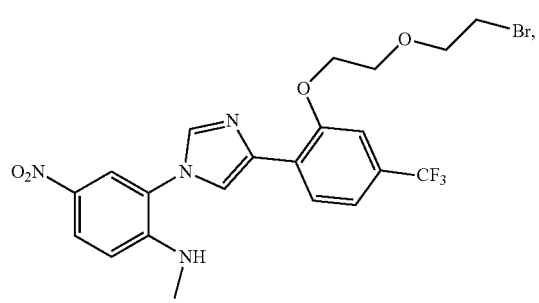
Compound 34
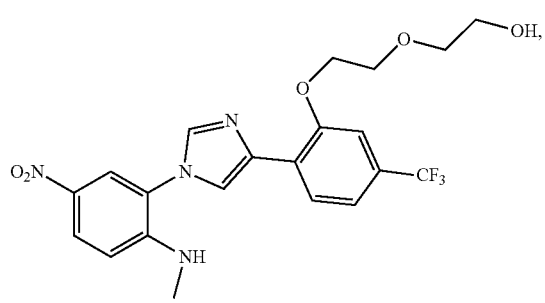
Compound 35
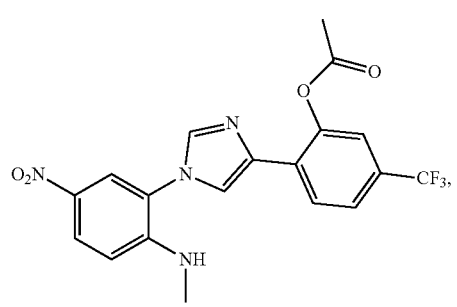
Compound 36
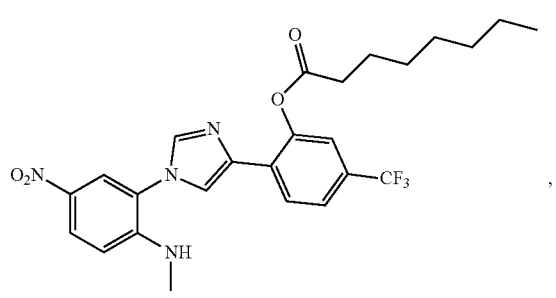

-continued
Compound 37
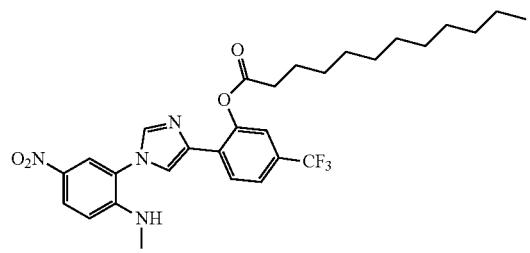
Compound 38
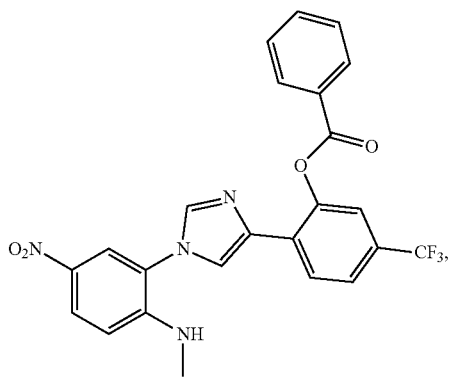
Compound 39
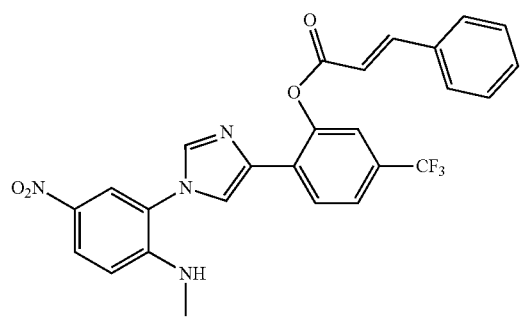
Compound 40
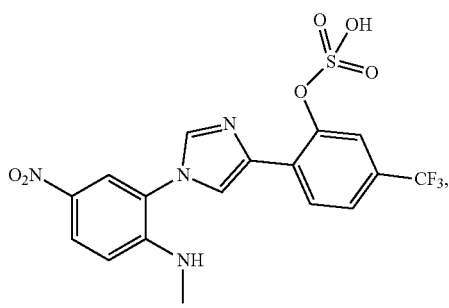
Compound 41
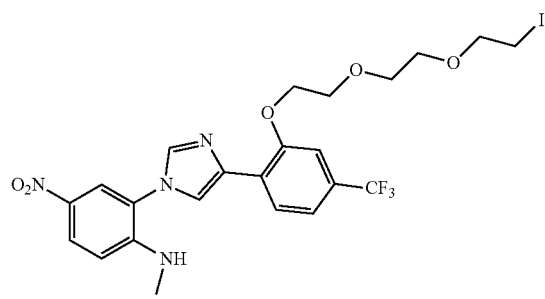
Compound 42
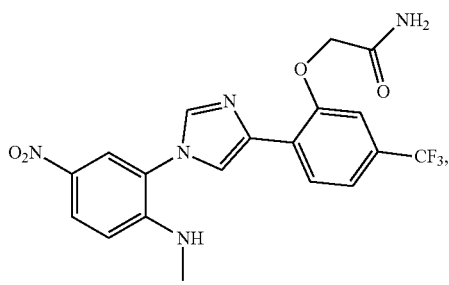
Compound 43
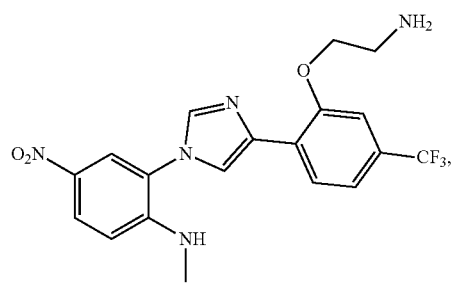

-continued
Compound 44
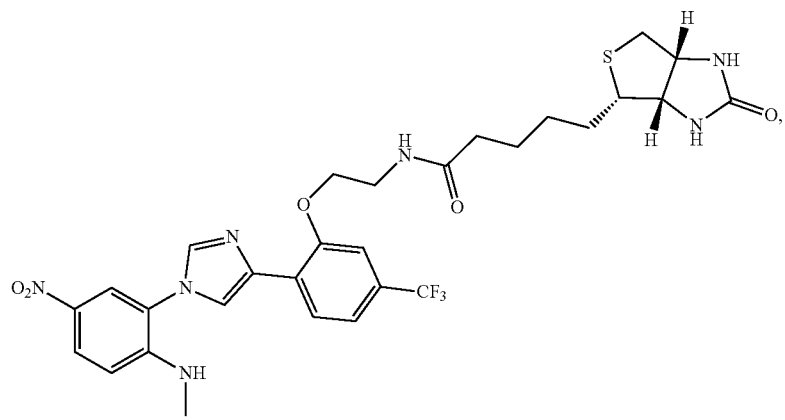
Compound 45
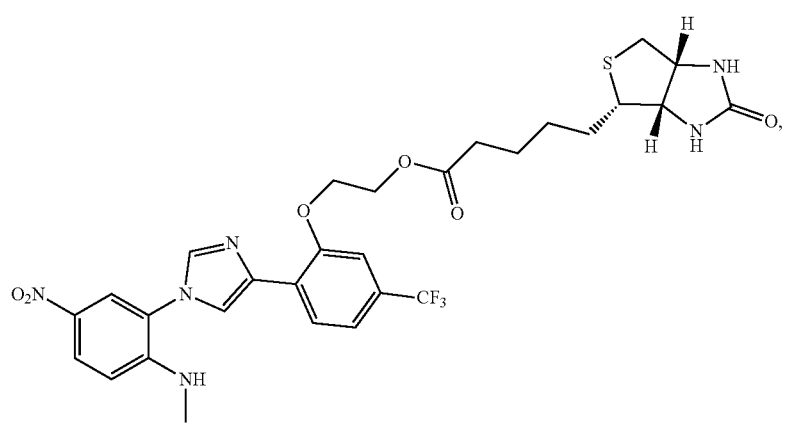
Compound 46
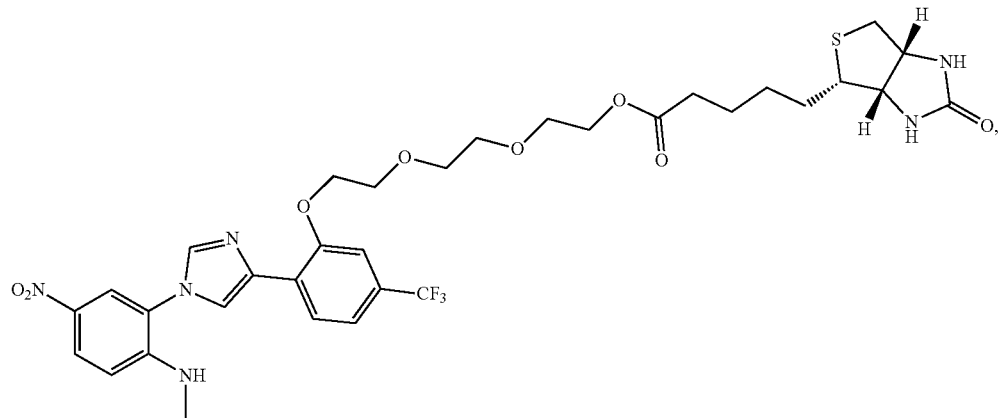
Compound 47
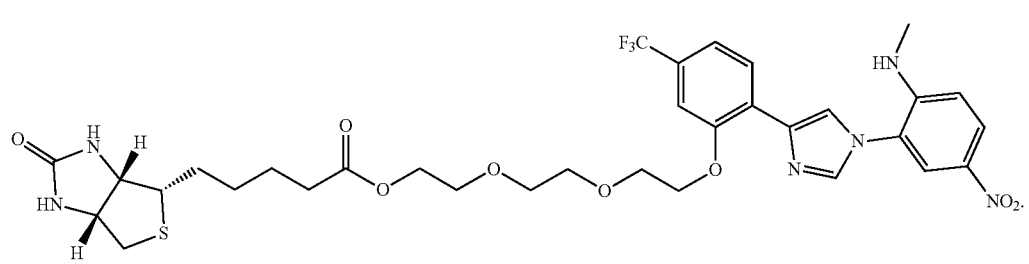

In another aspect, the present invention provides a process for the preparation of the compound of Formula I-1, wherein the process for the preparation of the compound of Formula I-1 comprises the following steps:

1) allowing compound A1

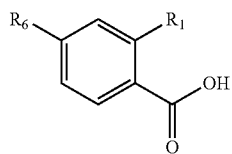

to react as catalyzed by methyllithium to obtain compound A2

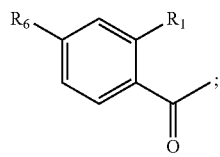

2) allowing the compound A2

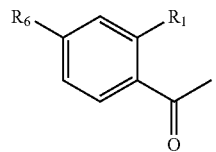

to react in the presence of tetrabutylammonium tribromide to obtain compound A3

3) reacting the compound A3

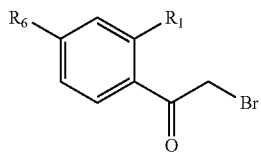

with compound A4

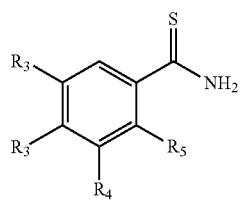

to obtain the compound represented by Formula I-1;
where, $R_1$ is selected from the group consisting of H, OH, $OCH_3$, $OCH_2CH_3$, $OCH_2C_6H_5$, $O(CH_2)_2Br$, $O(CH_2)_3Br$, $O(CH_2)_2O(CH_2)_2Br$, $O(CH_2)_2(CH_2)_2OH$, $OCOCH_3$, $OCO(CH_2)_6CH_3$, $OCO(CH_2)_{10}CH_3$, $OCOC_6H_5$, $OCOCH=CHC_6H_5$, $OSO_3H$, $O(CH_2)_2O(CH_2)_2O(CH)_2I$, $OCH_2CONH_2$, $O(CH_2)_2NH_2$, $O(CH_2)_2NH$-Biotin, $O(CH_2)_2O$-Biotin, and $O(CH_2)_2O(CH_2)_2O$-Biotin, $R_2$ is selected from the group consisting of H, $NO_2$, $CH_3$, $CF_3$, $SO_2CH_3$, $COOCH_3$, $CONHCH_3$, or $—N^+O—O^-$, $R_3$ is selected from the group consisting of H, $NO_2$, $OCH_3$, or $CF_3$, $R_3$ is selected from the group consisting of H, $CF_3$, or Cl, $R_5$ is selected from the group consisting of H, Cl, $CF_3$, or $NHCH_3$, and $R_6$ is selected from the group consisting of H, $OCF_3$, $CF_3$, or CN; V is either C or N, W is selected from either CH or N, X is C, Y is either CH or N, and Z is either CH or S.

A process for the preparation of the compounds 1-20 (as summarized in FIG. 1), comprising the following steps:

1) allowing compound A1

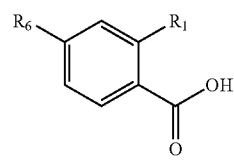

to react as catalyzed by methyllithium to obtain compound A2

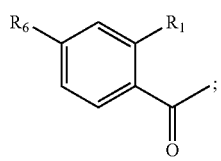

2) allowing the compound A2

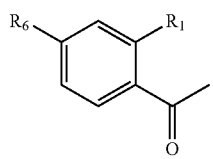

to react in the presence of tetrabutylammonium tribromide to obtain compound A3

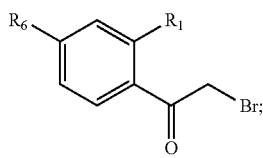

3) reacting the compound A3

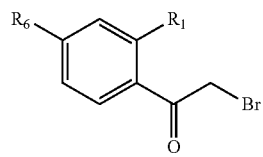

with compound A4

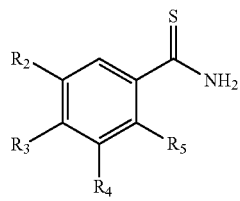

to obtain the compounds 1-20;
wherein, $R_1$-$R_6$ in the intermediate compounds A1, A2, A3 and A4 for preparing the compounds and their corresponding product compounds 1-20 are as follows:
1: $R_1$=$R_3$=$R_4$=H, $R_2$=$NO_2$, $R_5$=Cl, $R_6$=$CF_3$;
2: $R_1$=$R_3$=$R_4$=H, $R_2$=$NO_2$, $R_5$=$NHCH_3$, $R_6$=$CF_3$;
3: $R_1$=$R_2$=$R_3$=$R_4$=$R_5$=H, $R_6$=$CF_3$;
4: $R_1$=$R_3$=$R_4$=$R_5$=H, $R_2$=$CF_3$, $R_6$=$CF_3$;
5: $R_1$=$R_2$=$R_4$=$R_5$=H, $R_5$=$CF_3$, $R_6$=$CF_3$;
6: $R_1$=$R_2$=$R_3$=$R_4$=H, $R_5$=$CF_3$, $R_6$=$CF_3$;
7: $R_1$=$R_3$=$R_5$=H, $R_2$=$R_4$=$CF_3$, $R_6$=$CF_3$;
8: $R_1$=$R_2$=$R_4$=$R_5$=H, $R_3$=$OCH_3$, $R_6$=$CF_3$;
9: $R_1$=$R_2$=$R_4$=$R_5$=H, $R_3$=$NO_2$, $R_6$=CF;
10: $R_1$=$R_3$=$R_4$=$R_5$=H, $R_2$=$CH_3$, $R_6$=$CF_3$;
11: $R_1$=OH, $R_2$=$NO_2$, $R_3$=$R_4$=H, $R_5$=Cl, $R_6$=$CF_3$;
12: $R_1$=OH, $R_2$=$NO_2$, $R_3$=$R_4$=H, $R_5$=$NHCH_3$, $R_6$=$CF_3$;
13: $R_1$=OH, $R_2$=$R_3$=$R_4$=$R_5$=H, $R_6$=$CF_3$;
14: $R_1$=OH, $R_2$=$CF_3$, $R_3$=$R_4$=$R_5$=H, $R_6$=$CF_3$;
15: $R_1$=OH, $R_2$=$R_4$=$R_5$=H, $R_3$=$CF_3$, $R_6$=$CF_3$;
16: $R_1$=OH, $R_2$=$R_3$=$R_4$=H, $R_5$=$CF_3$, $R_6$=$CF_3$;
17 $R_1$=OH, $R_2$=$R_4$=$CF_3$, $R_3$=$R_5$=H, $R_6$=$CF_3$;
18: $R_1$=OH, $R_2$=$R_4$=$R_5$=H, $R_3$=$OCH_3$, $R_6$=$CF_3$;
19: $R_1$=OH, $R_2$=$R_4$=$R_5$=H, $R_3$=$NO_2$, $R_6$=$CF_3$;
20: $R_1$=OH, $R_2$=$CH_3$, $R_3$=$R_4$=$R_5$=H, $R_6$=$CF_3$.

In another aspect, the present invention provides a process for the preparation of the compound of Formula I-2, which comprises the following steps:
1) allowing compound A1

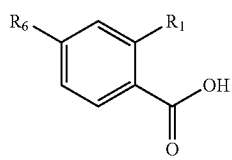

to react as catalyzed by methyllithium to obtain compound A2 allowing the compound A2

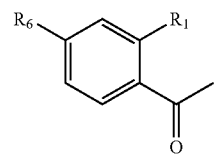

to react in the presence of tetrabutylammonium tribromide to obtain compound A3

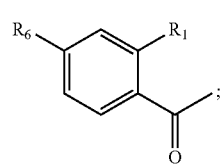

2) allowing compound B1

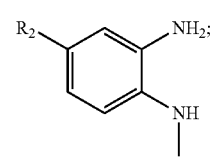

to react in methylamine to give an amino-substituted compound B2 reducing the compound B2 to obtain compound B3 or aminomethylating compound B5

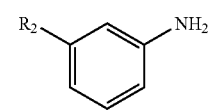

to obtain the compound B3;

3) reacting compound B3 with triethyl orthoformate to form a ring to obtain compound B4

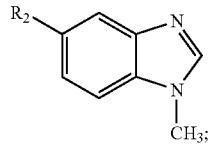

4) reacting the compound B4 with the compound A3 to obtain compound B6

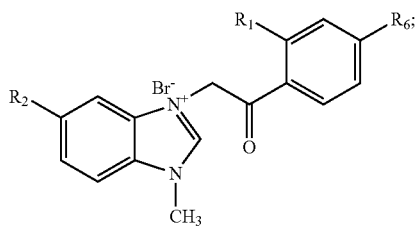

5) refluxing the compound B6 under acidic conditions to obtain the compound represented by Formula I-2;

optionally, the product obtained in step 5) is subjected to chloro-substitution in the presence of thionyl chloride to obtain the compound represented by Formula I-2;

where, $R_1$ is selected from the group consisting of H, OH, $OCH_3$, $OCH_2CH_3$, $OCH_2C_6H_5$, $O(CH_2)_2Br$, $O(CH_2)_3Br$, $O(CH_2)_2O(CH_2)_2Br$, $O(CH_2)_2O(CH_2)_2OH$, $OCOCH_3$, $OCO(CH_2)_6CH_3$, $OCO(CH_2)_{10}CH_3$, $OCOC_6H_5$, $OCOCH=CHC_6H_5$, $OSO_3H$, $O(CH_2)_2O(CH_2)_2O(CH)_2I$, $OCH_2CONH_2$, $O(CH_2)_2NH_2$, $O(CH_2)_2NH$-Biotin, $O(CH_2)_2O$-Biotin, or $O(CH_2)_2O(CH_2)_2O$-Biotin, $R_2$ is selected from the group consisting of H, $NO_2$, $CH_3$, $CF_3$, $SO_2CH_3$, $COOCH_3$, $CONHCH_3$, or —$N^+$—O—$O^-$, and $R_6$ is selected from the group consisting of H, $OCF_3$, $CF_3$, or CN;

preferably, $R_1$, $R_2$ and $R_6$ in the intermediate compounds A3, B1, B2, B3, B4 and B5 for preparing the compounds and their corresponding product compounds 21-27 are as follows:

21: $R_1$=OH, $R_6$=$OCF_3$, $R_2$=$NO_2$;
22: $R_1$=OH $R_6$=$CF_3$, $R_2$=$NO_2$;
23: $R_1$=OH, $R_6$=$CF_3$, $R_2$=$SO_2CH_3$;
24: $R_1$=OH, $R_6$=$CF_3$, $R_2$=$COOCH_3$;
25: $R_1$=OH, $R_6$=$CF_3$, $R_2$=$CONHCH_3$;
26: $R_1$=OH, $R_6$=$CF_3$, $R_2$=$NO_2$
27: $R_1$=H, $R_6$=CN, $R_2$=$NO_2$.

In another aspect, the present invention provides a process for the preparation of the compound represented by Formula I-2 (as summarized in FIG. 2), which comprises the following steps:

1) preparing compound 22

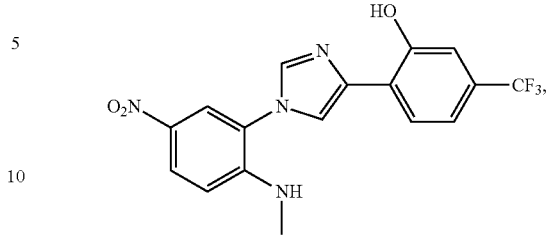

2) reacting the compound 22 with $R_7X$ to obtain compound

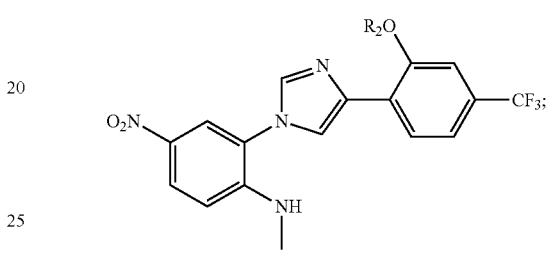

the $R_7$ is selected from $CH_3$, $CH_3CH_2$, $C_6H_5CH_2$, $C_2H_4Br$, $C_3H_6Br$, $(CH_2)_2(CH_2)_2Br$, $(CH_2)_2O(CH_2)_2OH$, $COCH_3$, $C_7H_{15}CO$, $C_{11}H_{23}CO$, $C_6H_5CO$, $C_6H_5CH=CHCO$, $SO_3H$, $(CH_2)_2O(CH_2)_2O(CH_2)_2I$, and $NH_2COCH$;

the X is halogen, and preferably Cl, Br, and I.

In the technical solution of the present invention, the process for the preparation of the compound I-2 comprises the following steps:

1) preparing compound 22

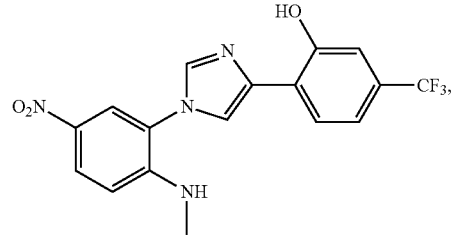

and reacting the compound 22 with 1,2-dibromoethane to obtain compound 31

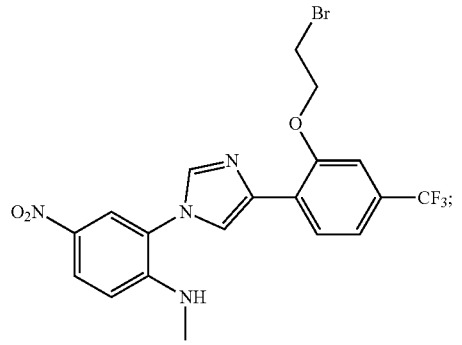

2) reacting the compound 31 with NH₃H₂O and KI to obtain compound 43

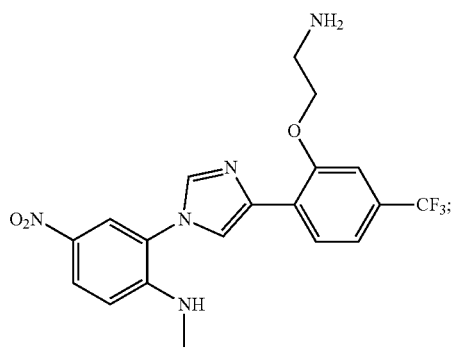 [SMILES: CNc1ccc([N+](=O)[O-])cc1-n1cnc(-c2ccc(C(F)(F)F)cc2OCCBr)c1]

optionally, reacting the compound 43 with compound

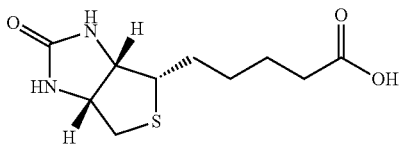 [SMILES: O=C(O)CCCC[C@@H]1SC[C@@H]2NC(=O)N[C@@H]21]

to obtain compound 44

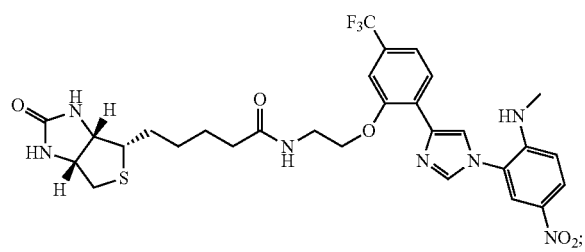 [SMILES: CNc1ccc([N+](=O)[O-])cc1-n1cnc(-c2ccc(C(F)(F)F)cc2OCCNC(=O)CCCC[C@@H]2SC[C@@H]3NC(=O)N[C@@H]32)c1]

or
2) reacting the compound 31 with biotin

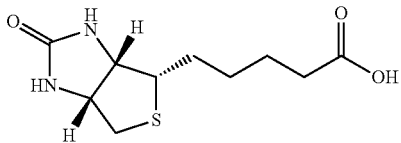 [SMILES: O=C(O)CCCC[C@@H]1SC[C@@H]2NC(=O)N[C@@H]21]

to obtain compound 45, 46 or 47

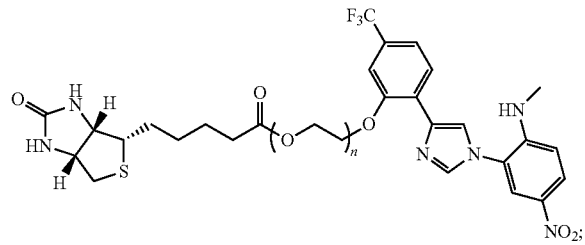

45: n = 1
46: n = 2
47: n = 3 or 2) reacting biotin with I(CH₂)₂O(CH₂)₂O(CH₂)₂I or T(CH₂)₂O(CH₂)₂I to obtain

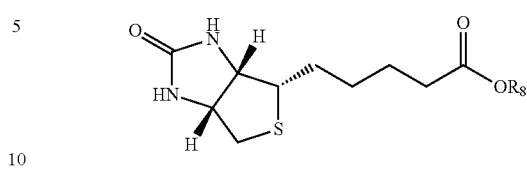

which then reacts with the compound 22 to obtain compound 45, 46 or 47;

where, $R_8$ is (CH₂)₂O(CH₂)₂O(CH₂)₂I or (CH₂)₂O(CH₂)₂I.

In another aspect, the present invention provides a pharmaceutical composition comprising the compound of the present invention or a pharmaceutically acceptable salt thereof, as well as a pharmaceutically acceptable carrier or excipient.

In another aspect, the present invention provides a use of the above compound in preparation of anti-inflammatory adjuvants, TLR1 or TLR2 agonists, and anti-tumor agents.

In still another aspect, the present invention provides a method for regulating the activity activation level of TLR1 and TLR2 alkaline phosphatases in vitro and in vivo, comprising administering the compound of Formula I to a subject.

The present invention provides uses of the compound represented by Formula I in TLR1, TLR2, etc.

The compounds 1-47 of the present invention can be structurally modified to obtain compounds with better activity and used to treat TLR1 and TLR2 related diseases.

A specific technical solution of the present invention provides a process for the preparation of the compound, which comprises the following steps:

1. 2-hydroxy-4-(trifluoromethyl)benzoic acid is dissolved in THF under ice bath, 1.6 M methyllithium is added thereto dropwise, and the reaction mixture is stirred at room temperature for 4 hours. Then it is quenched with distilled water and adjusted to pH=7 with dilute HCl and extracted with ethyl acetate. The collected organic layer is dried over anhydrous Na₂SO₄, concentrated under reduced pressure, and purified by column chromatography (petroleum ether) to obtain corresponding products including oily 1-(2-hydroxy-4-(trifluoromethyl)phenyl)ethanone.

2. The oily 1-(2-hydroxy-4-(trifluoromethyl)phenyl)ethanone is dissolved in MeOH and DCM at room temperature. Detrabutylammonium tribromide is dissolved in DCM and then added into the aforementioned mixture solution dropwise to react at room temperature for 24 hours. After the reaction is completed, the organic phase is spin-dried under reduced pressure and purified by column chromatography (petroleum ether-ethyl acetate=8:1) to obtain 2-bromo-1-(2-hydroxy-4-(trifluoromethyl)phenyl)ethanone as yellow oil.

3. Thiobenzamides with different substituents and bromoacetophenone are refluxed in EtOH overnight, and then cooled; crystals are precipitated and suction filtration is conducted.

4. The substituted aniline is dissolved in DMF, triethyl orthoformate is added thereto to form a precipitate in concentrated HCl, substituted imidazole is obtained after filtering and recrystallized in methanol ice bath.

5. The substituted imidazole and bromoacetophenone are refluxed in MeOH as a solvent for 12 hours; after the solvent is spun off, the mixture is treated ultrasonically with acetone to obtain a precipitate which is then filtered out and dried, and then the filter cake is recrystallized in methanol to obtain a substituted bromide salt.

6. The substituted bromide salt is refluxed overnight in acetic acid and ammonium acetate, distilled water is added thereto to obtain a precipitate, which is then filtered to obtain 1,4-diphenyl-1H-imidazole.

7. 1,4-Diphenyl-1H-imidazole reacts with a base in an aprotic solvent and a halogenated alkane is added thereto to prepare an intermediate with 1,4-diphenyl-1H-imidazole as the core.

8. The intermediate with 1,4-diphenyl-1H-imidazole as the core reacts with a base in an aprotic solvent, and biotin is added to prepare biotin labeled with 1,4-diphenyl-1H-imidazole as the core.

Some of the compounds shown above can activate TLR1/2 receptors in a dose-dependent manner.

The compound 22 of the present invention can be used to make TLR1 and TLR2 related adjuvants, drugs and the like. Using modern common pharmaceutical preparation methods, the compound can be made into injections, tablets, powders, granules, and capsules which are conveniently administrated, wherein the mass percentage content of the compound of the present invention in the drug is 1-20%.

The above-mentioned drugs in various dosage forms can be prepared according to conventional methods in the pharmaceutical field.

DETAILED DESCRIPTION OF THE EMBODIMENTS

Figure 1:
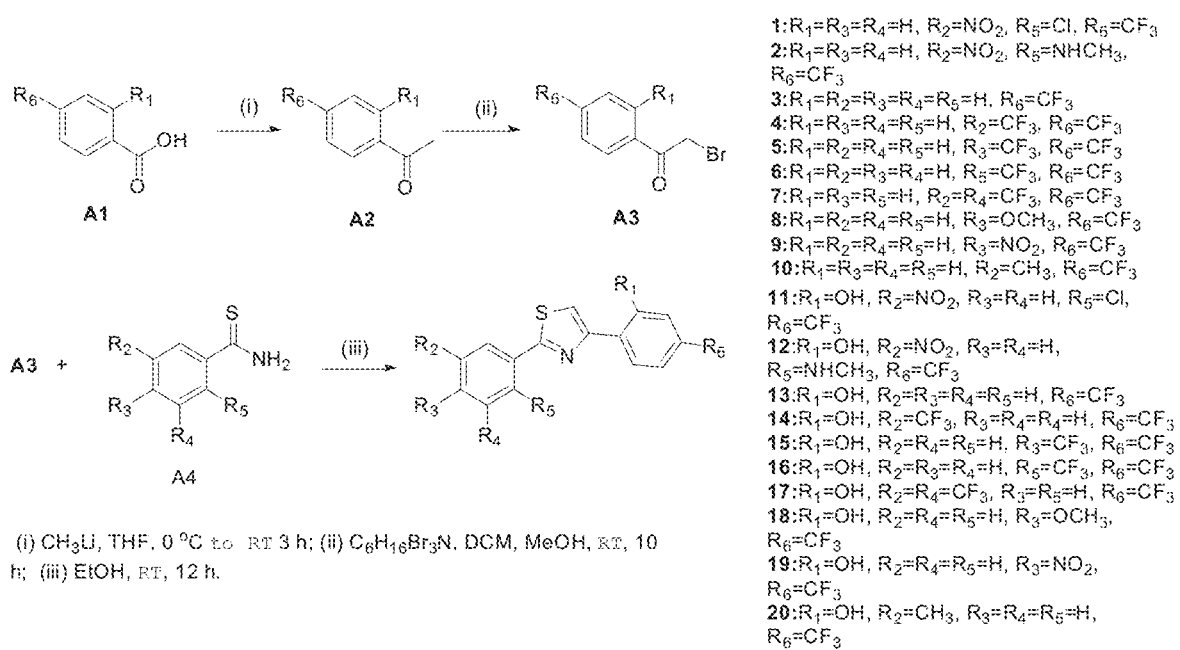
FIG. 1: Reaction scheme for the preparation of compounds 1-20.
Figure 2:
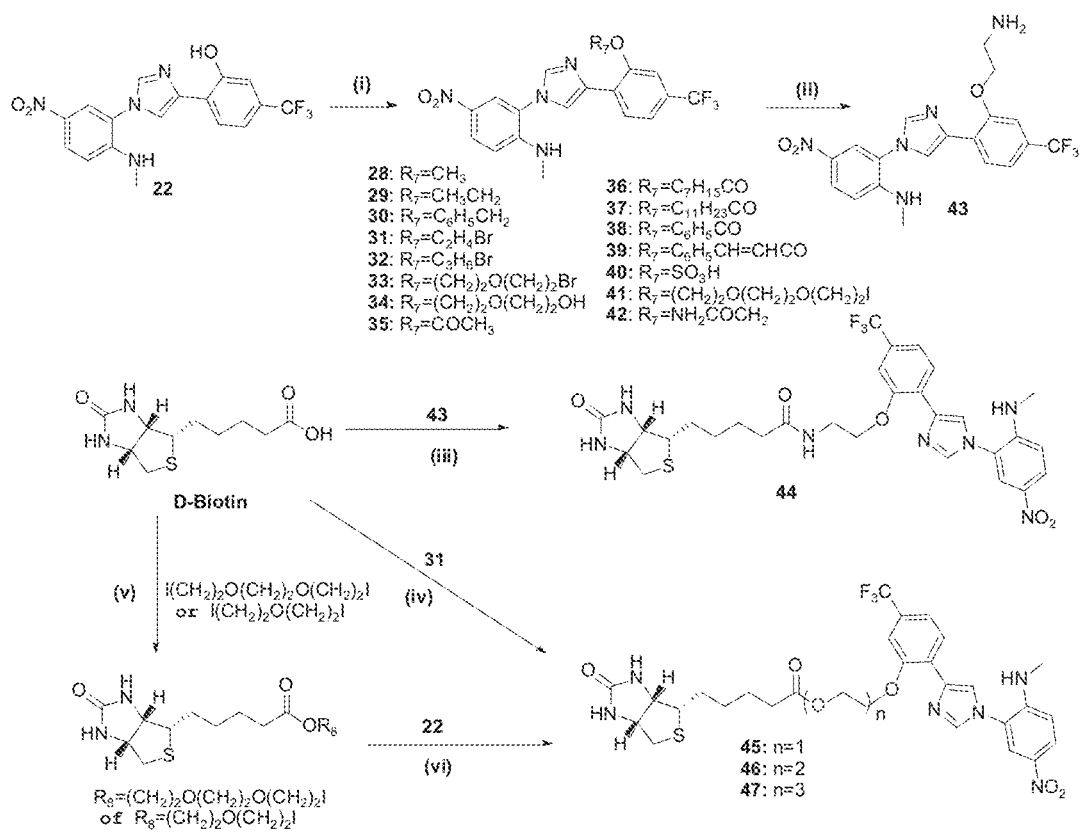
FIG. 2: Reaction scheme for the preparation of compounds 28-47.
Figure 3:
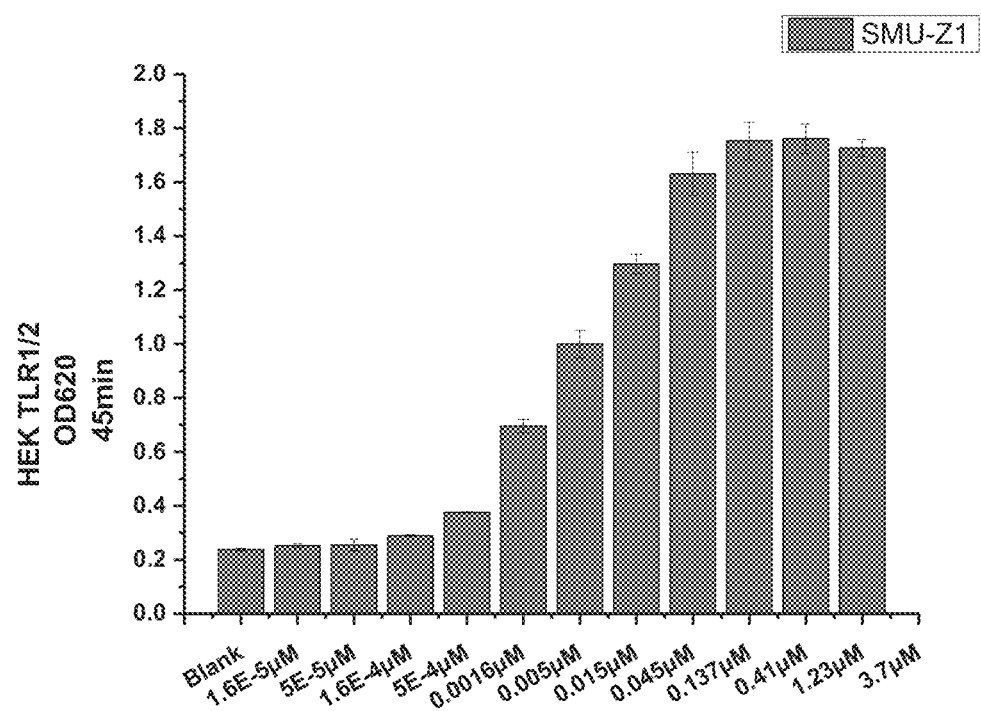
FIG. 3: Compound 22 activates TLR1/2 activity in a concentration-dependent manner.

In order to better understand the present invention, the present invention will be further described below in conjunction with specific embodiments, but the protection scope of the present invention is not limited thereto.

Example 1: Preparation of Compound 1

Preparation of
1-(2-hydroxy-4-(trifluoromethyl)phenyl)ethanone 2-hydroxy-4-(trifluoromethyl)benzoic acid (1.0 g, 4.85 mmol) was dissolved in THF (10 mL) in an ice bath, 1.6 M (10 mL) methyllithium was added thereto dropwise, and the reaction mixture was stirred at room temperature for 4 hours. Then it was quenched with distilled water, adjusted to pH=7 with dilute HCl and extracted with ethyl acetate (3×50 mL). The collected organic layer was dried over anhydrous $Na_2SO_4$, concentrated under reduced pressure, and purified by column chromatography (petroleum ether) to obtain an oily product 1-(2-hydroxy-4-(trifluoromethyl)phenyl)ethanone (750 mg, 75.8%).

Preparation of 2-bromo-1-(2-hydroxy-4-(trifluoromethyl)phenyl)ethanone

The oily 1-(2-hydroxy-4-(trifluoromethyl)phenyl)ethanone (1.0 g, 0.0049 mmol) was dissolved in MeOH (12 mL) and DCM (6 mL) at room temperature. Tetrabutylammonium tribromide (2.59 g, 0.0054 mmol) was dissolved in DCM (12 mL) and added into the aforementioned mixed solution dropwise to react at room temperature for 24 hours. After the reaction was completed, the organic phase was spin-dried under reduced pressure and purified by column chromatography (petroleum ether-ethyl acetate) to obtain yellow oily 2-bromo-1-(2-hydroxy-4-(trifluoromethyl)phenyl)ethanone (1.32 g, 95%).

Preparation of Compound 1

2-chloro-5-nitrothiobenzamide (243 mg, 1.12 mmol) and 2-bromo-1-(4-(trifluoromethyl)phenyl)ethanone (300 mg, 1.12 mmol) were dissolved in EtOH (5 mL). The reaction solution was allowed to react for 4 hours under reflux, and the reaction was monitored by TLC. After the reaction was completed, the mixture was cooled to produce a precipitate, and the precipitate was filtered out to obtain compound 2-(2-chloro-5-nitrophenyl)-5-(4-(trifluoromethyl)phenyl)thiazole with a yield of 100%.

Example 2: Preparation of Compound 2

The compound 2-(2-chloro-5-nitrophenyl)-5-(4-(trifluoromethyl)phenyl)thiazole (300 mg, 0.78 mmol) and methylamine 40% aqueous solution (263 mg, 3.9 mmol) were dissolved in EtOH (15 mL) to react at room temperature, and the reaction was monitored by TLC. After the reaction was completed, the reaction mixture was extracted with ethyl acetate (3×50 mL) and then washed with water to remove methylamine. The collected organic layer was dried over anhydrous $Na_2SO_4$, concentrated under reduced pressure, and purified by column chromatography (petroleum ether-ethyl acetate=4:1) to obtain N-methyl-4-nitro-2-(5-(4-(trifluoromethyl)phenyl)thiazol-2-yl)aniline with a yield of 100%.

The compound 2-(methylamino)-5-nitrobenzothioamide (211.2 mg, 1 mmol) and 2-bromo-1-(4-(trifluoromethyl)phenyl)ethanone (300 mg, 1.12 mmol) were dissolved in EtOH (5 mL). The reaction solution was allowed to react for 4 hours under reflux, and the reaction was monitored by TLC. After the reaction was completed, the reaction mixture was cooled to produce a precipitate, and the precipitate was filtered out to obtain compound 2-(2-methylamino-5-nitrophenyl)-5-O-(trifluoromethyl)phenyl)thiazole with a yield of 100%.

Example 3: Preparation of Compounds 3-20

In Example 3, compounds 3-20 were prepared respectively. The preparation steps of the compounds 3-2.0 are the same as those in the preparation of compound 1, except that the raw materials used are different. The differences are shown in Table 1 below:

TABLE 1

| The difference between compounds 3-20 and compound 1 | |
| --- | --- |
| Compound No. | Difference from compound 1 in steps |
| 3 | Replace 2-chloro-5-nitrothiobenzamide with thiobenzamide |
| 4 | Replace 2-chloro-5-nitrothiobenzamide with 3-(trifluoromethyl)thiobenzamide |
| 5 | Replace 2-chloro-5-nitrothiobenzamide with 4-(trifluoromethyl)thiobenzamide |

TABLE 1-continued

The difference between compounds 3-20 and compound 1

| Compound No. | Difference from compound 1 in steps |
|---|---|
| 6 | Replace 2-chloro-5-nitrothiobenzamide with 2-(trifluoromethyl)thiobenzamide |
| 7 | Replace 2-chloro-5-nitrothiobenzamide with 3-bis(trifluoromethyl)thiobenzamide |
| 8 | Replace 2-chloro-5-nitrothiobenzamide with 4-methoxythiobenzamide |
| 9 | Replace 2-chloro-5-nitrothiobenzamide with 4-nitrothiobenzamide |
| 10 | Replace 2-chloro-5-nitrothiobenzamide with 3-methylthiobenzamide |
| 11 | Replace 2-bromo-1-(4-(trifluoromethyl)phenyl)ethanone with 2-bromo-1-(2-hydroxy-4-(trifluoromethyl)phenyl)ethanone |
| 12 | Replace 2-chloro-5-nitrothiobenzamide with 2-(methylamino)-5-nitrothiobenzamide, and replace 2-bromo-1-(4-(trifluoromethyl)phenyl)ethanone with 2-bromo-1-(2-hydroxy-4-(trifluoromethyl)phenyl)ethanone |
| 13 | Replace 2-chloro-5-nitrothiobenzamide with thiobenzamide, and replace 2-bromo-1-(4-(trifluoromethyl)phenyl)ethanone with 2-bromo-1-(2-hydroxy-4-(trifluoromethyl)phenyl)ethanone |
| 14 | Replace 2-chloro-5-nitrothiobenzamide with 3-(trifluoromethyl)thiobenzamide, and replace 2-bromo-1-(4-(trifluoromethyl)phenyl)ethanone with 2-bromo-1-(2-hydroxy-4-(trifluoromethyl)phenyl)ethanone |
| 15 | Replace 2-chloro-5-nitrothiobenzamide with 4-(trifluoromethyl)thiobenzamide, and replace 2-bromo-1-(4-(trifluoromethyl)phenyl)ethanone with 2-bromo-1-(2-hydroxy-4-(trifluoromethyl)phenyl)ethanone |
| 16 | Replace 2-chloro-5-nitrothiobenzamide with 2-(trifluoromethyl)thiobenzamide, and replace 2-bromo-1-(4-(trifluoromethyl)phenyl)ethanone with 2-bromo-1-(2-hydroxy-4-(trifluoromethyl)phenyl)ethanone |
| 17 | Replace 2-chloro-5-nitrothiobenzamide with 3,5-bis(trifluoromethyl)thiobenzamide, and replace 2-bromo-1-(4-(trifluoromethyl)phenyl)ethanone with 2-bromo-1-(2-hydroxy-4-(trifluoromethyl)phenyl)ethanone |
| 18 | Replace 2-chloro-5-nitrothiobenzamide with 4-methoxythiobenzamide, and replace 2-bromo-1-(4-(trifluoromethyl)phenyl)ethanone with 2-bromo-1-(2-hydroxy-4-(trifluoromethyl)phenyl)ethanone |
| 19 | Replace 2-chloro-5-nitrothiobenzamide with 4-nitrothiobenzamide, and replace 2-bromo-1-(4-(trifluoromethyl)phenyl)ethanone with 2-bromo-1-(2-hydroxy-4-(trifluoromethyl)phenyl)ethanone |
| 20 | Replace 2-chloro-5-nitrothiobenzamide with 3-methylthiobenzamide, and replace 2-bromo-1-(4-(trifluoromethyl)phenyl)ethanone with 2-bromo-1-(2-hydroxy-4-(trifluoromethyl)phenyl)ethanone |

Example 4: Preparation of Compound 22

1. Preparation of 1-(2-hydroxy-4-(trifluoromethyl)phenyl)ethanone 2-hydroxy-4-(trifluoromethyl)benzoic acid (1.0 g, 4.85 mmol) was dissolved in THF (10 mL) in an ice bath, 1.6 M (10 mL) methyllithium was added thereto dropwise, and the reaction mixture was stirred at room temperature for 4 hours. Then it was quenched with distilled water and adjusted to pH=7 with dilute HCl and extracted with ethyl acetate (3-50 mL). The collected organic layer was dried over anhydrous $Na_2SO_4$, concentrated under reduced pressure, and purified by column chromatography (petroleum ether) to obtain an oily product 1-(2-hydroxy-4-(trifluoromethyl)phenyl)ethanone (750 mg, 75.8%).

2. Preparation of 2-bromo-1-(2-hydroxy-4-(trifluoromethyl)phenyl)ethanone

The oily 1-(2-hydroxy-4-(trifluoromethyl)phenyl)ethanone (1.0 g, 0.0049 mmol) was dissolved in MeOH (12 mL) and DCM (6 mL) at room temperature. Tetrabutylammonium tribromide (2.59 g, 0.0054 mmol) was dissolved in DCM (12 mL) and then added into the aforementioned mixed solution dropwise to react at room temperature for 24 hours. After the reaction was completed, the organic phase was spin-dried under reduced pressure and purified by column chromatography (petroleum ether-ethyl acetate) to obtain yellow oily 2-bromo-1-(2-hydroxy-4-(trifluoromethyl)phenyl)ethanone (1.32 g, 95%).

3. Preparation of 1-methyl-5-nitro-1H-benzo[d]imidazole

N1-methyl-4-nitrobenzene-1,2-diamine (251 mg, 1.5 mmol) was dissolved in DMF (4 mL), and triethyl orthoformate (10 mL) was added thereto to form a pale yellow precipitate in concentrated HCl (12 N solution, 167 μL, 5 mmol), filtering was conducted to obtain 1-methyl-5-nitro-1H-benzo[d]imidazole (90 mg, 33.7%) which was then recrystallized in a methanol ice bath.

4. Preparation of 3-(2-(2-hydroxy-4-(trifluoromethyl)phenyl)-2-oxoethyl)-1-methyl-5-nitro-1H-benzo[d]imidazo-3-ium bromide 2-bromo-1-(2-hydroxy-4-(trifluoromethyl)phenyl)ethanone (566 mg, 2 mmol) and 1-methyl-5-nitro-1H-benzo[d]imidazole (354 mg, 2 mmol) were refluxed in MeOH (20 mL) as a solvent for 12 hours. The reaction mixture was spin-dried to remove the solvent and then treated ultrasonically with acetone to obtain a precipitate. The precipitate was filtered out and dried, and then the filter cake was recrystallized in methanol to prepare 3-(2-(2-hydroxy-4-(trifluoromethyl)phenyl)-2-oxoethyl)-1-methyl-5-nitro-1H-benzo[d]imidazo-3-ium bromide (920 mg, 100%).

5. Preparation of 2-(1-(2-(methylamino)-5-nitrophenyl)-1H-imidazol-4-yl)-5-(trifluoromethyl)phenol 3-(2-(2-hydroxy-4-(trifluoromethyl)phenyl)-2-oxoethyl)-1-methyl-5-nitro-1H-benzo[d]imidazo-3-ium bromide (920 mg, 12 mmol) was refluxed overnight in acetic acid (10 mL) and ammonium acetate (770 mg, 10 mmol). After the reaction was completed, distilled water (100 mL) was added thereto to precipitate a yellow solid. After suction filtration, the solid was recrystallized to give pure 2-(1-(2-(methylamino)-5-nitrophenyl)-1H-imidazol-4-yl)-5-(trifluoromethyl)phenol (378 mg, 50%).

Example 5: Preparation of Compounds 21, 23, 24, 25

TABLE 2

The difference between compounds 21, 23, 24, 25 and compound 22

| Compound No. | Difference from compound 22 in steps |
|---|---|
| 21 | Replace the preparation of 2-bromo-1-(2-hydroxy-4-(trifluoromethyl)phenyl)ethanone with 2-bromo-1-(4-(trifluoromethoxy)phenyl)ethanone |

TABLE 2-continued

The difference between compounds 21, 23, 24, 25 and compound 22

| Compound No. | Difference from compound 22 in steps |
|---|---|
| 23 | Replace N1-methyl-4-nitrobenzene-1,2-diamine with N1-methyl-4-(methylsulfonyl)benzene-1,2-diamine |
| 24 | Replace N1-methyl-4-nitrobenzene-1,2-diamine with methyl 3-amino-4-(methylamino)benzoate |
| 25 | Replace N1-methyl-4-nitrobenzene-1,2-diamine with 3-amino-N-methyl-4-(methylamino)benzamide |

Example 6: Preparation of Compound 26

2-(1-(2-(methylamino)-5-nitrophenyl)-1H-imidazol-4-yl)-5-(trifluoromethyl)phenol (30 mg, 0.08 mmol) was dissolved in thionyl chloride (4 mL) to react at room temperature. The reaction was monitored by TLC. After the reaction was completed, the reaction mixture was spin-dried to remove thionyl chloride, and purified by column chromatography (petroleum ether-ethyl acetate=2:1) to obtain yellow 2-(1-(3-chloro-2-(methylamino)-5-nitrophenyl)-1H-imidazol-4-yl)-5-(trifluoromethyl)phenol (750 mg, 75.8%).

Example 7: Preparation of Compound 27

TABLE 3

The difference between compound 27 and compound 26

| Compound No. | Difference from compound 26 in steps |
|---|---|
| 27 | Replace the preparation of 2-bromo-1-(2-hydroxy-4-(trifluoromethyl)phenyl)ethanone with 4-(2-bromoacetyl)benzonitrile |

Example 8: Preparation of Compound 28

2-(1-(2-(methylamino)-5-nitrophenyl)-1H-imidazol-4-yl)-5-(trifluoromethyl)phenol (30 mg, 0.082 mmol) and $K_2CO_3$ (101.8 mg, 0.738 mmol) were dissolved in acetone (3 ml) and stirred for 20 minutes. Then methyl iodide (34.9 mg, 0.246 mmol) was added thereto to react at 50° C. and the reaction was monitored by TLC. After the reaction was completed, it was quenched with water and extracted with ethylacetate (3×50 mL). The collected organic layer was dried over anhydrous $Na_2SO_4$, concentrated under reduced pressure, and purified by column chromatography (petroleum ether-ethyl acetate=1:1) to obtain yellow 2-(4-(2-methoxy-4-(trifluoromethyl)phenyl)-H-imidazol-1-yl)-N-methyl-4-nitroaniline (28.6 mg, 92%).

Example 9: Preparation of Compounds 29, 30, 31, 32, 33, 34, 40, 41, 42

TABLE 4

The difference between compounds 29, 30, 31, 32, 33, 34, 40, 41, 42 and compound 28

| Compound No. | Difference from compound 28 in steps |
|---|---|
| 29 | Replace $CH_3I$ with $CH_3CH_2I$ |
| 30 | Replace $CH_3I$ with $C_6H_5CH_2I$ |
| 31 | Replace $CH_3I$ with $C_2H_4Br_2$ |
| 32 | Replace $CH_3I$ with $C_3H_6Br_2$ |
| 33 | Replace $CH_3I$ with $(CH_2)_2O(CH_2)_2Br_2$ |
| 34 | Replace $CH_3I$ with $Cl(CH_2)_2O(CH_2)_2OH$ |
| 40 | Replace $CH_3I$ with $SO_3$—Py |
| 41 | Replace $CH_3I$ with $(CH_2)_2O(CH_2)_2O(CH_2)_2I_2$ |
| 42 | Replace $CH_3I$ with $NH_2COCH_2Cl$ |

Example 10: Preparation of Compound 35

2-(1-(2-(methylamino)-5-nitrophenyl)-1H-imidazol-4-yl)-5-(trifluoromethyl)phenol (10 mg, 0.026 mmol) was dissolved in DCM (20 ml), triethylamine (200 uL) was added thereto, the reaction mixture was stirred in an ice bath for 10 minutes, and then acetyl chloride (2 ml) was added thereto dropwise. The reaction was monitored by TLC. After the reaction was completed, the reaction mixture was spin-dried to remove the solvent, and purified by column chromatography (petroleum ether-ethyl acetate=1:1) to obtain yellow (1-(2-(methylamino)-5-nitrophenyl)-1H-imidazol-4-yl)-5-(trifluoromethyl)phenyl acetate (9.2 mg, 85%).

Example 11: Preparation of Compounds 36, 37, 38, 39

TABLE 5

The difference between compounds 36, 37, 38, 39 and compound 35

| Compound No. | Difference from compound 35 in steps |
|---|---|
| 36 | Replace $CH_3COCl$ with $C_7H_{15}COCl$ |
| 37 | Replace $CH_3COCl$ with $C_{11}H_{23}COCl$ |
| 38 | Replace $CH_3COCl$ with $C_6H_5COCl$ |
| 39 | Replace $CH_3COCl$ with $C_7H_{15}COCl$ |

Example 12: Preparation of Compound 43

2-(4-(2-(2-bromoethoxy)-4-(trifluoromethyl)phenyl)-1H-imidazol-1-yl)-N-methyl-4-nitroaniline (35 mg, 0.082 mmol), potassium iodide (68 mg, 0.41 mmol) was dissolved in THF (4 ml) and 30% ammonia (4 mL), and refluxed overnight in a sealed state. The reaction was monitored by TLC. After the reaction was completed, it was extracted and purified by column chromatography (dichloromethane-methanol=9:1) to obtain yellow 2-(4-(3-(2-aminoethoxy)-4-(trifluoromethyl)phenyl)-1H-imidazol-1-yl)-N-methyl-4-nitroaniline (24.5 mg, 71%).

Example 13: Preparation of Compound 44

Biotin (34.8 mg, 0.14 mmol) was dissolved in DMF (4 mL), HATU (80.94 mg, 0.213 mmol) and DIPEA (2 mL) were added thereto, with stirring for 30 minutes. Then 2-(4-(3-(2-aminoethoxy)-4-(trifluoromethyl)phenyl)-1H-imidazol-1-yl)-N-methyl-4-nitroaniline (30 mg, 0.071 mmol) was added thereto. The reaction mixture was kept at 45° C. overnight and the reaction was monitored by TLC. After the reaction was completed, it was extracted and purified by column chromatography (ethyl acetate-methanol=9:1) to obtain yellow N-(2-(2-(1-(2-(methylamino)-5-nitrophenyl)-1H-imidazol-4-yl)-5-(trifluoromethyl)phenoxy)ethyl)-5-((3AS, 4S, 6AR)-2-oxohexahydro-1H-thieno[3,4-d]imidazol-4-yl)pentanamide (42.76 mg, 93%).

Example 14: Preparation of Compounds 45, 46, 47

TABLE 6

The difference between compounds 45, 46, 47 and compound 35

| Compound No. | Difference from compound 44 in steps |
|---|---|
| 45 | Replace joining chain $(CH_2)_2NH_2$ with $CH_2CH_2$ |
| 46 | Replace joining chain $(CH_2)_2NH_2$ with $(CH_2)_2O(CH_2)_2$ |
| 47 | Replace joining chain $(CH_2)_2NH_2$ with $(CH_2)_2O(CH_2)_2O(CH_2)_2$ |

Example 15: Structural Verification of the Compound

Compound 1

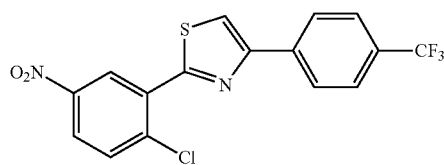

2-(2-chloro-5-nitrophenyl)-5-(4-(trifluoromethyl)phenyl)thiazole

White solid (276.2 mg, 64.1%). m. p. 169.2-170.2° C. H NMR (400 MHz, CDCl3) δ 9.34 (d, J=2.8 Hz, 1H), 8.23 (dd, J=8.8, 2.8 Hz, 1H), 8.16 (d, J=8.1 Hz, 2H), 7.86 (s, 1H), 7.74 (dd, J=12.4, 8.5 Hz, 3H). $^{13}$C NMR (101 MHz, CDCl$_3$) δ 99.97, 160.97, 153.95, 146.81, 137.96, 136.88, 132.89, 131.83, 130.50, 126.68, 125.84, 124.31, 117.21. MS (EST-TOF) for $C_{16}H_8ClF_3N_2O_2S$ [M+H]$^+$ calculated 385.76, found 385.96.

Compound 2

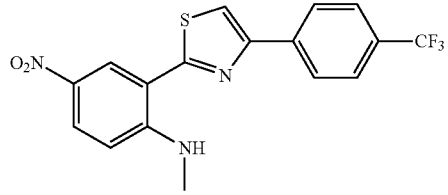

N-methyl-4-nitro-2-(5-(4-(trifluoromethyl)phenyl)thiazol-2-yl)aniline

Yellow solid (284.9 mg, 96.3%). m.p. 145.3-145.9° C. $^1$H NMR (400 MHz, DMSO) δ 9.40 (d, J=5.0 Hz, 1H), 8.57-8.37 (m, 2H), 8.24 (d, J=8.2 Hz, 2H), 8.19 (dd, J=9.3, 2.5 Hz, 1H), 7.85 (d, J=8.3 Hz, 2H), 6.97 (d, J=9.5 Hz, 1H), 3.14 (d, 3H). $^{13}$C NMR (101 MHz, DMSO) δ 167.39, 152.95, 151.80, 137.26, 135.79, 127.21, 126.27, 125.45, 116.73, 113.68, 111.54, 30.35. MS (ESI-TOF) for $C_{17}H_{12}F_3N_3O_2S$ [M+H]$^+$ calculated 380.36, found 380.32.

Compound 3

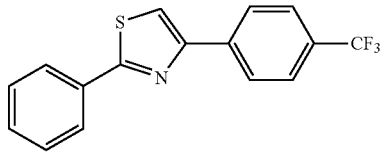

2-phenyl-4-(4-(trifluoromethyl)phenyl)thiazole

White solid (299.2 mg, 98.2%). m.p. 126.1-127.0° C. $^1$H NMR (400 MHz, CDCl$_3$) δ 8.14 (d, J=8.2 Hz, 2H), 8.07 (dd, J=7.4, 2.1 Hz, 2H), 7.73 (d, J=8.3 Hz, 2H), 7.61 (s, 1H), 7.50 (dd, J=5.0, 2.3 Hz, 3H). $^{13}$C NMR (101 MHz, CDCl$_3$) δ 168.34, 154.65, 137.65, 133.41, 130.28, 130.03, 129.70, 128.96, 126.60, 125.68, 122.84, 114.32. MS (ESI-TOF) for $C_{16}H_{10}F_3NS$ [M+H]$^+$ calculated 306.32, found 305.59.

Compound 4

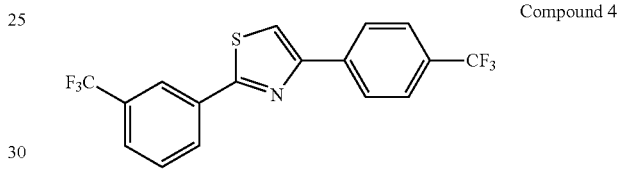

2-(3-(trifluoromethyl)phenyl)-4-(4-(trifluoromethyl)phenyl)thiazole

White solid (302.1 mg, 80.9%). m.p. 91.7-95.2° C. $^1$H NMR (400 MHz, CDCl3) δ 8.14 (d, J=8.2 Hz, 2H), 8.07 (dd, J=7.4, 2.1 Hz, 2H), 7.73 (d, J=8.3 Hz, 2H), 7.61 (s, 1H), 7.50 (dd, J=5.0, 2.3 Hz, 3H). $^{13}$C NMR (101 MHz, CDCl3) δ 168.34, 154.65, 137.65, 133.41, 130.28, 130.03, 129.70, 128.96, 126.60, 125.68, 122.84, 114.32. MS (ESI-TOF) for $C_{17}H_9F_6NS$ [M+H]$^+$ calculated 374.32, found 375.11.

Compound 5

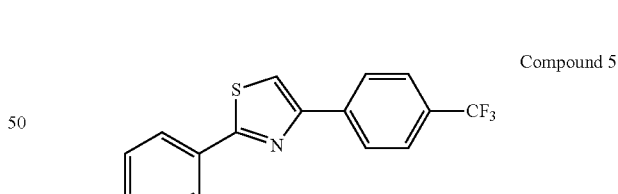

2,5-bis(4-(trifluoromethyl)phenyl)thiazole

White solid (282 mg, 75.6%). m.p. 126.3-127.8° C. $^1$H NMR (400 MHz, CDCl3) δ 8.14 (dd, J=17.3, 8.1 Hz, 96H), 7.74 (t, J=7.3 Hz, 96H), 7.65 (s, 18H), 7.28 (s, 3H). $^{13}$C NMR (101 MHz, CDCl3) δ 166.40, 155.17, 137.27, 136.42, 131.69, 130.32, 126.77, 125.94, 125.76, 122.75, 115.24. MS (ESI-TOF) for $C_{17}H_9F_6NS$ [M+H]$^+$ calculated 374.32, found 374.29.

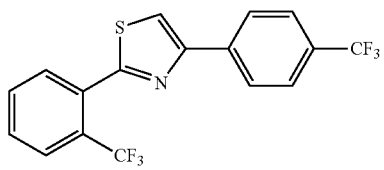

Compound 6

2-(2-(trifluoromethyl)phenyl)-5-(4-(trifluoromethyl)phenyl)thiazole

White solid (303.1 mg, 81.2%). m.p. 123.4-126.2° C. $^1$H NMR (400 MHz, CDCl3) δ 8.11 (d, J=8.2 Hz, 2H), 7.89 (d, J=7.5 Hz, 1H), 7.82-7.56 (m, 6H). $^{13}$C NMR (101 MHz, CDCl3) δ 164.64, 154.31, 137.39, 132.40, 132.14, 131.73, 130.17, 129.84, 129.05, 128.74, 127.00, 126.64, 125.71, 125.49, 124.98, 122.79, 122.26, 116.25. MS (ESI-TOF) for $C_{17}H_9F_6NS$ [M+H]$^+$ calculated 374.32, found 374.78.

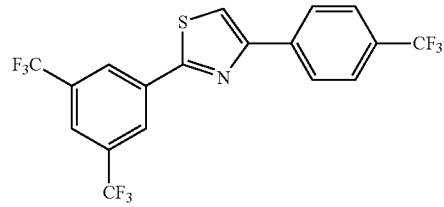

Compound 7

2-(3,5-bis(trifluoromethyl)phenyl)-4-(4-(trifluoromethyl)phenyl)thiazole

White solid (319.1 mg, 72.3%). m.p. 125.7-126.4° C. $^1$H NMR (400 MHz, CDCl3) δ 8.49 (s, 2H), 8.15 (d, J=8.1 Hz, 2H), 7.98 (s, 1H), 7.84-7.66 (m, 3H). $^{13}$C NMR (101 MHz, CDCl3) δ 164.58, 155.51, 136.84, 135.20, 132.72, 130.59, 130.27, 127.03, 126.49, 125.78, 125.38, 124.32, 123.38, 122.68, 121.61, 118.89, 115.69. MS (ESI-TOF) for $C_{18}H_8F_9NS$ [M+H]$^+$ calculated 440.31, found 440.95.

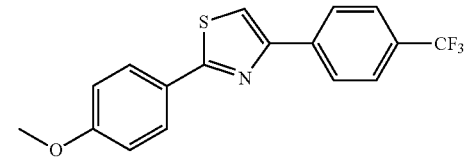

Compound 8

4-(4-methoxyphenyl)-2-(3-(trifluoromethyl)phenyl)thiazole

White solid (320.58 mg, 95.6%). m.p. 128.7-129.9° C. $^1$H NMR (400 MHz, CDCl3) δ 8.12 (d, J=7.7 Hz, 2H), 8.05-7.91 (m, 2H), 7.71 (d, J=8.0 Hz, 2H), 7.52 (s, 1H), 7.06-6.88 (m, 2H), 3.90 (d, 3H). $^{13}$C NMR (101 MHz, CDCl$_3$) δ 168.20, 161.33, 154.38, 137.76, 128.09, 126.52, 125.60, 114.27, 113.45, 55.37. MS (ESI-TOF) for $CH_2F_3NOS$ [M+H]$^+$ calculated 336.34, found 337.08.

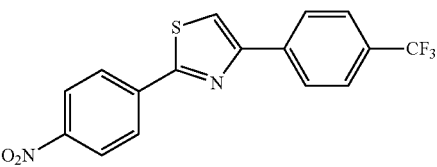

Compound 9

4-(4-nitrophenyl)-2-(3-(trifluoromethyl)phenyl)thiazole

Yellow solid (349.6 mg, 99.8%). m.p. 120.8-121.5° C. $^1$H NMR (400 MHz, DMSO) δ 8.51 (s, 1H), 8.26 (dd, J=33.7, 6.1 Hz, 6H), 7.80 (d, J=6.3 Hz, 2H). $^{13}$C NMR (101 MHz, DMSO) δ 165.01, 154.53, 148.36, 137.46, 127.50, 127.04, 126.03, 124.75, 123.24, 119.59. MS (ESI-TOF) for $C_{16}H_9F_3N_2O_2S$ [M+H]$^+$ calculated 351.32, found 351.32.

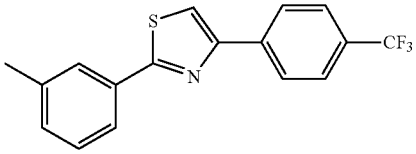

Compound 10

2-(m-tolyl)-4-(4-(trifluoromethyl)phenyl)-2,5-dihydrothiazole

White solid (299.8 mg, 93.9%). m.p. 94.8-95.5° C. $^1$H NMR (400 MHz, CDCl3) δ 8.13 (d, J=8.0 Hz, 2H), 7.90 (s, 1H), 7.85 (d, J=7.7 Hz, 1H), 7.72 (d, J=8.2 Hz, 2H), 7.59 (s, 1H), 7.39 (t, J=7.6 Hz, 1H), 7.30 (d, J=7.6 Hz, 1H), 2.48 (s, 3H). $^{13}$C NMR (101 MHz, CDCl3) δ 168.59, 154.58, 138.77, 137.69, 133.31, 131.11, 129.99, 128.86, 127.13, 126.56, 125.63, 123.84, 122.85, 114.23, 21.33. MS (ESI-TOF) for $C_{17}H_{14}F_3NS$ [M+H]$^+$ calculated 322.36, found 333.01.

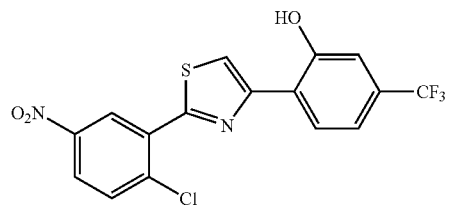

Compound 11

2-(2-(2-chloro-5-nitrophenyl)thiazol-5-yl)-5-(trifluoromethyl)phenol

White solid (560.4 mg, 81.6%). m.p. 187.4-188.6° C. $^1$H NMR (400 MHz, CDCl$_3$) δ 11.54 (s, 1H), 8.93 (d, J=2.7 Hz, 1H), 8.30 (dd, J=8.8, 2.7 Hz, 1H), 7.94 (s, 1H), 7.80 (d, J=8.8 Hz, 2H), 7.35 (d, J=1.2 Hz, 1H), 7.28 (s, 1H), 7.21 (dd, J=8.2, 1.2 Hz, 1H). $^{13}$C NMR (101 MHz, CDCl3) δ 156.09, 132.32, 126.75, 125.44, 125.10, 116.47. MS (ESI-TOF) for $C_{16}H_8ClF_3N_2O_3S$ [M+H]$^+$ calculated 401.76, found 401.21.

Compound 12

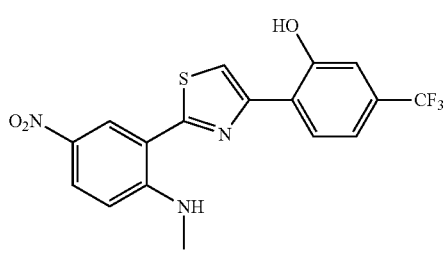

2-(2-(2-(methylamino)-5-nitrophenyl)thiazol-5-yl)-5-(trifluoromethyl)phenol

Yellow solid (192.3 mg, 45.8%). m.p. 194.6-198.7° C. $^1$H NMR (400 MHz, DMSO) δ 11.08 (s, 1H), 9.50 (d, J=4.8 Hz, 1H), 8.48 (d, J=2.2 Hz, 1H), 8.39 (s, 1H), 8.27-8.10 (m, 2H), 7.29 (d, J=7.3 Hz, 2H), 6.96 (d, J=9.4 Hz, 1H), 3.13 (d, 3H). $^{13}$C NMR (101 MHz, DMSO) δ 165.55, 155.57, 151.83, 149.65, 135.73, 130.27, 127.26, 125.34, 123.97, 119.10, 116.21, 113.81, 112.90, 111.35, 30.28. MS (ESI-TOF) for $C_{17}H_{12}F_3N_3O_3S$ [M+H]$^+$ calculated 396.36, found 397.25.

Compound 13

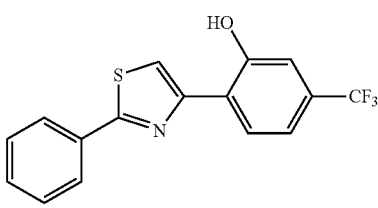

2-(2-phenylthiazol-4-yl)-5-(trifluoromethyl)phenol

White solid (427.6 mg, 90.7%). m.p. 132.5-134.2° C. $^1$H NMR (400 MHz, CDCl3) δ 12.13 (s, 1H), 7.97-7.88 (m, 2H), 7.69 (d, J=8.1 Hz, 1H), 7.60 (s, 1H), 7.50 (s, 3H), 7.32 (s, 1H), 7.14 (d, J=8.1 Hz, 1H). $^{13}$C NMR (101 MHz, CDCl3) δ 168.17, 156.17, 153.04, 131.79, 130.96, 129.17, 126.40, 125.17, 122.51, 122.31, 120.09, 115.78, 115.09, 113.31. MS (ESI-TOF) for $C_{16}H_{10}F_3NOS$ [M+H]$^+$ calculated 322.32, found 322.30.

Compound 14

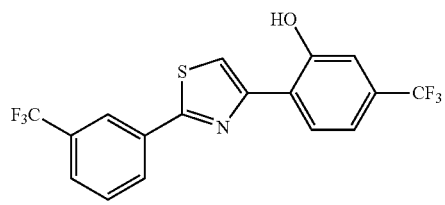

5-(trifluoromethyl)-2-(2-(3-(trifluoromethyl)phenyl)thiazol-4-yl)phenol

White solid (302.5 mg, 74.6%). m.p. 108.5-109.8° C. $^1$H NMR (400 MHz, CDCl$_3$) δ 11.81 (s, 1H), 8.16 (d, J=7.6 Hz, 2H), 7.76 (dd, J=13.9, 9.4 Hz, 3H), 7.67 (t, J=7.8 Hz, 1H), 7.33 (s, 1H), 7.18 (d, J=8.2 Hz, 1H). $^{13}$C NMR (101 MHz, CDCl$_3$) δ 166.43, 156.05, 153.60, 132.60, 129.89, 129.51, 127.42, 126.56, 123.17, 122.15, 119.81, 115.97, 115.16, 114.23. MS (ESI-TOF) for $C_{17}H_9F_6NOS$ [M+H]$^+$ calculated 390.31, found 390.39.

Compound 15

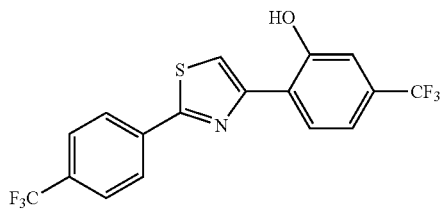

5-(trifluoromethyl)-2-(2-(4-(trifluoromethyl)phenyl)thiazol-5-yl)phenol

White solid (387.6 mg, 70.3%). m. p. 138.6-139.2° C. $^1$H NMR (400 MHz, CDCl$_3$) δ 11.80 (s, 1H), 8.09 (d, J=8.1 Hz, 2H), 7.88-7.69 (m, 4H), 7.34 (s, 1H), 7.19 (d, J=8.2 Hz, 1H). $^{13}$C NMR (101 MHz, CDCl3) δ 166.36, 156.11, 153.77, 134.92, 132.75, 132.34, 132.01, 126.74, 126.45, 125.05, 122.35, 119.80, 116.03, 115.22, 114.50. MS (ESI-TOF) for $C_{17}H_9F_6NOS$ [M+H]$^+$ calculated 390.31, found 389.14.

Compound 16

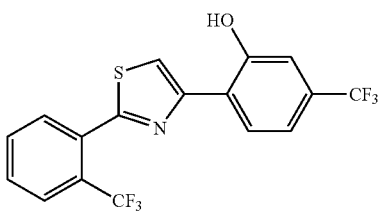

5-(trifluoromethyl)-2-(2-(2-(trifluoromethyl)phenyl)thiazol-5-yl)phenol

White solid (391.3 mg, 71.2%). m.p. 138.9-140.7° C. $^1$H NMR (400 MHz, CDCl3) δ 11.68 (s, 1H), 7.91 (d, J=7.1 Hz, 1H), 7.83 (s, 1H), 7.78 (d, J=8.2 Hz, 1H), 7.75-7.64 (m, 3H), 7.32 (s, 1H), 7.18 (d, J=8.2 Hz, 1H). $^{13}$C NMR (101 MHz, CDCl$_3$) δ 164.76, 156.17, 153.10, 132.11, 132.02, 130.44, 127.25, 126.54, 119.92, 115.79, 115.41, 115.35. MS (ESI-TOF) for $C_1H_9F_6NOS$ [M+H]$^+$ calculated 390.31, found 391.21.

Compound 17

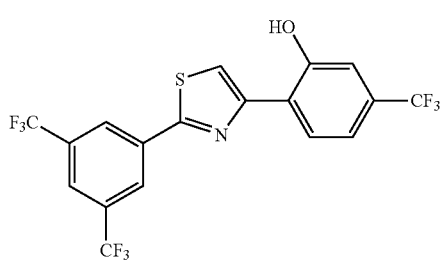

2-(2-(3,5-bis(trifluoromethyl)phenyl)thiazol-4-yl)-5-(trifluoromethyl)phenol White solid (117.2 mg, 75.6%). m.p. 157.6-158.2° C. $^1$H NMR (400 MHz, CDCl3) δ 11.48 (s, 1H), 8.36 (s, 2H), 8.03 (s, 1H), 7.82 (s, 1H), 7.77 (d, J=8.2 Hz, 1H), 7.33 (s, 1H), 7.20 (d, J=8.1 Hz, 1H). $^{13}$C NMR (101 MHz, CDCl3) δ 164.62, 155.91, 154.13, 133.82, 133.51, 133.17, 132.49, 132.26, 126.71, 126.24, 124.96, 124.08, 122.25, 121.37, 119.52, 118.66, 116.18, 115.24. MS (ESI-TOF) for $C_{18}H_8F_9NOS$ [M+H]$^+$ calculated 456.31, found 456.02.

Compound 18

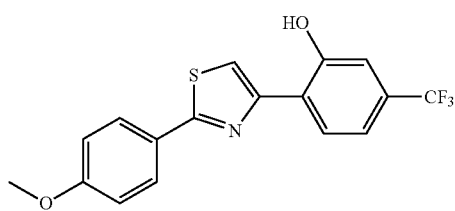

2-(4-(4-methoxyphenyl)thiazol-2-yl)-5-(trifluoromethyl)phenol

White solid (342.7 mg, 86.4%). m.p. 146.2-147.3° C. $^1$H NMR (400 MHz, CDCl3) δ 12.25 (s, 1H), 7.91 (d, J=8.5 Hz, 2H), 7.74 (d, J=8.2 Hz, 1H), 7.58 (s, 1H), 7.32 (s, 1H), 7.16 (d, J=8.1 Hz, 1H), 7.02 (d, J=8.6 Hz, 2H), 3.91 (s, 3H). $^{13}$C NMR (101 MHz, CDCl3) δ 168.10, 161.84, 156.19, 152.75, 131.49, 128.02, 126.37, 124.73, 120.24, 115.76, 115.06, 115.02, 114.50, 112.29, 55.42. MS (ESI-TOF) for $C_7H_{12}F_3NO_2S$ [M+H]$^+$ calculated 352.34, found 351.94.

Compound 19

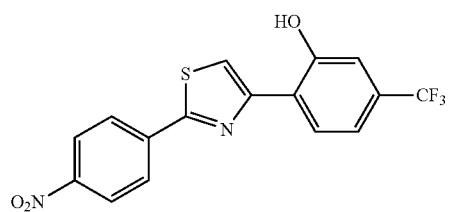

2-(4-(4-nitrophenyl)thiazol-2-yl)-5-(trifluoromethyl)phenol

Yellow solid (186.5 mg, 90.7%). m.p. 144.9-145.3° C. $^1$H NMR (400 MHz, DMSO) δ 11.16 (s, 1H), 8.54 (d, J=4.3 Hz, 1H), 8.46-8.39 (m, 1H), 8.40-8.33 (m, 2H), 8.33-8.23 (m, 2H), 7.30 (s, 2H). $^{13}$C NMR (101 MHz, DMSO) δ 163.54, 157.58, 157.48, 155.61, 151.53, 148.49, 138.56, 132.26, 130.40, 129.76, 127.70, 124.95, 124.00, 122.18, 116.10, 113.10. MS (ESI-TOF) for $C_{16}H_9F_3N_2OS$ [M+H]$^+$ calculated 367.31, found 368.55.

Compound 20

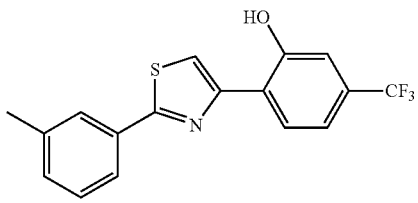

2-(2-(m-tolyl)-2,5-dihydrothiazol-4-yl)-5-(trifluoromethyl)phenol

White solid (277.6 mg, 69.4%). m.p. 100.7-101.1° C. $^1$H NMR (400 MHz, CDCl3) δ 12.17 (s, 1H), 7.78 (d, J=6.7 Hz, 3H), 7.65 (d, J=6.1 Hz, 1H), 7.46-7.35 (m, 1H), 7.33 (dd, J=13.6, 9.7 Hz, 2H), 7.18 (d, J=7.8 Hz, 1H), 2.48 (d, 3H). $^{13}$C NMR (101 MHz, CDCl$_3$) δ 168.41, 156.18, 152.96, 139.07, 131.77, 129.06, 126.91, 126.39, 125.18, 123.65, 122.47, 120.15, 115.77, 115.06, 113.16, 21.30. MS (ESI-TOF) for $C_{17}H_{14}F_3NOS$ [M+H]$^+$ calculated 378.36, found 377.66.

Compound 21

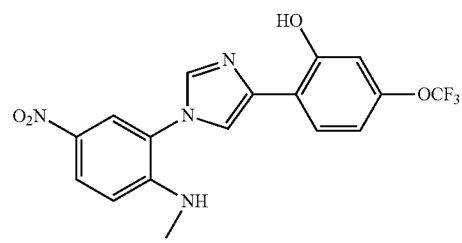

2-(1-(2-(methylamino)-5-nitrophenyl)-1H-imidazol-4-yl)-5-(trifluoromethoxy)phenol Yellow solid (203 mg, 86%). m.p. 194.4-195.1° C. $^1$H NMR (400 MHz, DMSO) δ 8.23 (dd, J=9.2, 2.5 Hz, 1H), 8.02 (d, J=2.7 Hz, 1H), 8.01-7.92 (m, 4H), 7.40 (dd, J=8.9, 0.9 Hz, 2H), 6.87 (d, J=9.4 Hz, 1H), 6.71 (q, J=4.5 Hz, 1H), 2.83 (s, 3H). $^{13}$C NMR (101 MHz, DMSO) δ 150.69, 147.38, 140.61, 139.15, 135.55, 134.04, 127.08, 126.54, 124.11, 121.89, 121.67, 121.63, 119.35, 118.28, 110.45, 30.27. MS (ESI-TOF) for $C_{17}H_1F_3N_4O_3$ [M+H]$^+$ calculated 379.31, found 378.02.

Compound 22

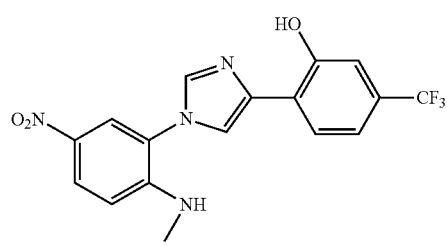

2-(1-(2-(methylamino)-5-nitrophenyl)-1H-imidazol-4-yl)-5-(trifluoromethyl)phenol Yellow solid (378 mg, 50%). $^1$H NMR (400 MHz, DMSO) δ 11.83 (s, 1H), 8.25 (dd, J=9.3, 2.6 Hz, 1H), 8.13 (d, J=1.0 Hz, 1H), 8.10-7.97 (m, 3H), 7.21 (d, J=8.0 Hz, 2H), 6.88 (d, J=9.4 Hz, H), 6.73 (d, J=4.8 Hz, 1H), 2.82 (d, 3H). $^{13}$C NMR (101 MHz, DMSO) δ 155.24), 150.74, 138.46, 137.90, 135.48, 128.30, 127.25, 126.96, 125.95, 124.43, 122.83, 121.23, 120.09, 115.89, 113.10, 110.44, 30.17. MS (ESI-TOF) for $C_7H_{13}F_3N_4O_3$ [M+H]$^+$ calculated 377.31, found 377.52.

Compound 23

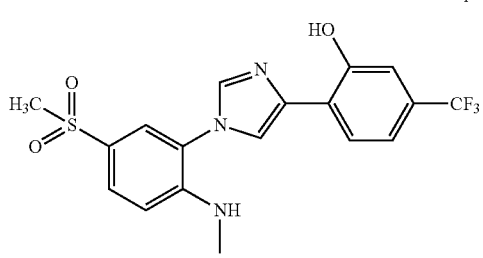

2-(1-(2-(methylamino)-5-(methylsulfonyl)phenyl)-1H-imidazol-4-yl)-5-(trifluoromethyl)phenol Pink solid (284 mg, 55%). m.p. 179.4-180.1° C. $^1$H NMR (400 MHz, DMSO) δ 11.90 (s, 1H), 8.22-7.96 (m, 3H), 7.83 (dd, J=8.8, 2.0 Hz, 1H), 7.67 (d, J=2.0 Hz, 1H), 7.22 (d, J=6.3 Hz, 2H), 6.91 (d, J=8.9 Hz, 1H), 6.23 (d, J=4.7 Hz, 1H), 3.17 (s, 3H), 2.78 (d, 3H). $^{13}$C NMR (101 MHz, DMSO) δ 155.34, 149.00, 138.52, 137.79, 130.07, 128.40, 128.09, 127.18, 126.93, 126.42, 125.97, 123.27, 122.74, 121.69, 120.00, 115.90, 113.18, 110.84, 44.61, 30.01. MS (ESI-TOF) for $C_8H_6F_3N_3O_3S$ [M+H]$^+$ calculated 412.40, found 412.44.

Compound 24

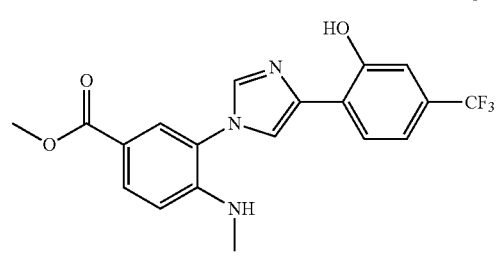

Methyl 3-(4-(2-hydroxy-4-(trifluoromethyl)phenyl)-1H-imidazol-1-yl)-4-(methylamino)benzoate Grey solid (64 mg, 34%). m.p. 182.2-183.5° C. $^1$H NMR (400 MHz, DMSO) δ 11.99 (s, 1H), 8.14-7.98 (m, 3H), 7.94 (dd, J=8.7, 1.5 Hz, H), 7.68 (d, J=1.8 Hz, 1H), 7.21 (d, J=6.9 Hz, 2H), 6.84 (d, J=8.8 Hz, 1H), 6.12 (d, J=4.8 Hz, 1H), 4.26 (d, J=7.1 Hz, 1H), 3.80 (s, 2H), 2.77 (d, 3H). $^{13}$C NMR (101 MHz DMSO) δ166.06, 155.36, 148.95, 137.76, 132.25, 129.03, 126.87, 122.68, 121.74, 119.95, 116.16, 113.17, 110.67, 79.59, 60.48, 51.96, 29.95, 14.65. MS (ESI-TOF) for $C_{19}H_{16}F_3N_3O_3$ [M+H]$^+$ calculated 392.34, found 392.39.

Compound 25

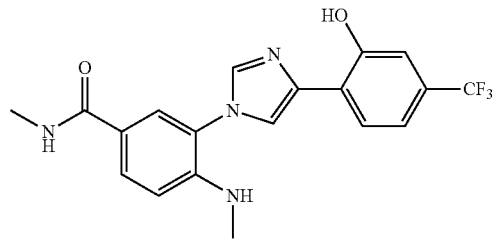

3-(4-(2-hydroxy-4-(trifluoromethyl)phenyl)-1H-imidazol-1-yl)-N-methyl-4-(methylamino)benzamide Grey solid (64 mg, 34%). m.p. 194.9-195.6° C. $^1$H NMR (400 MHz, DMSO) δ 12.00 (s, 1H), 8.19 (d, J=4.5 Hz, 1H), 8.13-7.97 (m, 3H), 7.88 (dd, J=8.6, 1.9 Hz, 1H), 7.70 (d, J=2.0 Hz, 1H), 7.21 (d, J=6.8 Hz, 2H), 6.80 (d, J=8.7 Hz, 1H), 5.78 (d, 1H), 2.75 (t, 6H). 13C NMR (101 MHz, DMSO) δ 166.00, 155.33, 147.17, 138.34, 137.79, 130.01, 128.26, 126.86, 125.97, 123.27, 122.73, 121.52, 120.09, 115.87, 113.13, 110.50, 30.07, 26.52. MS (ESI-TOF) for $C_{19}H_{17}F_3N_4O_2$ [M+H]$^+$ calculated 391.36, found 391.06.

Compound 26

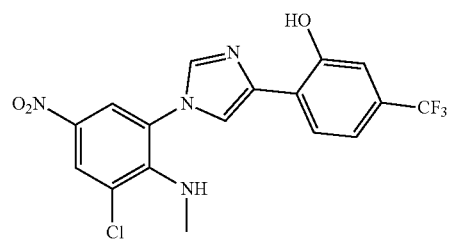

2-(1-(3-chloro-2-(methylamino)-5-nitrophenyl)-1H-imidazol-4-yl)-5-(trifluoromethyl)phenol Yellow solid (28.39 mg, 86%). m.p. 130.8-131.9° C. $^1$H NMR (400 MHz, DMSO) δ 11.53 (s, 1H), 8.31 (d, J=2.7 Hz, 1H), 8.21 (d, J=1.1 Hz, 1H), 8.16-8.06 (m, 3H), 7.21 (d, J=6.4 Hz, 2H), 6.87 (d, J=5.3 Hz, 1H), 2.40 (d, 3H). $^{13}$C NMR (101 MHz, DMSO) δ 155.06, 147.76, 139.87, 137.31, 135.04, 128.39, 128.08, 127.21, 126.37, 125.78, 122.93, 120.51, 120.11, 115.95, 112.88, 30.06. MS (ESI-TOF) for $C_{17}H_{12}ClF_3N_4O_3$ [M+H]$^+$ calculated 411.75, found 411.83.

Compound 27

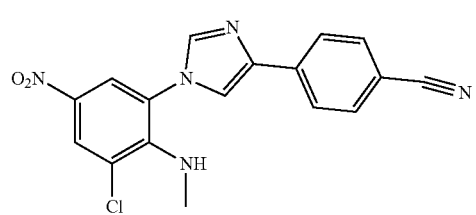

4-(1-(3-chloro-2-(methylamino)-5-nitrophenyl)-1H-imidazol-4-yl)benzonitrile

Yellow solid (34.2 mg, 62%). m. p. 210.8-212.6° C. $^1$H NMR (400 MHz, DMSO) δ 8.31 (d, J=2.5 Hz, 1H), 8.25 (s, 1H), 8.11 (s, 1H), 8.08 (d, J=2.4 Hz, 1H), 8.02 (d, J=8.2 Hz, 2H), 7.85 (d, J=8.2 Hz, 2H), 6.89 (s, 1H), 2.41 (s, 3H). $^{13}$C NMR (101 MHz, DMSO) 147.70, 141.57, 139.64, 138.83, 135.03, 133.09, 126.26, 125.77, 125.39, 122.46, 120.56, 120.08, 119.55, 109.23, 30.20. MS (ESI-TOF) for $C_{17}H_2C_1N_5O_2$ [M+H]$^+$ calculated 354.76, found 355.23.

Compound 28

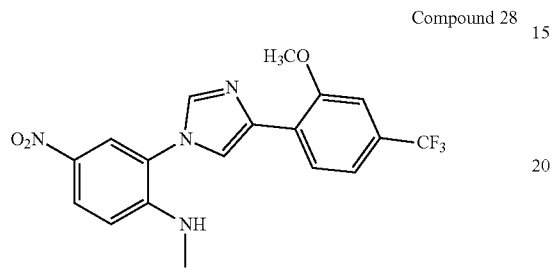

2-(4-(2-methoxy-4-(trifluoromethyl)phenyl)-1H-imidazol-1-yl)-N-methyl-4-nitroaniline Yellow solid (28.6 mg, 92%). m.p. 201.5-202.2° C. $^1$H NMR (400 MHz, DMSO) δ 8.39 (d, J=8.0 Hz, 1H), 8.23 (dd, J=9.3, 2.7 Hz, 1H), 8.01 (d, J=2.7 Hz, 1H), 7.97 (d, J=1.2 Hz, 1H), 7.88 (d, J=1.1 Hz, 1H), 7.40 (d, J=8.2 Hz, 1H), 7.35 (s, 1H), 6.87 (d, J=9.4 Hz, 1H), 6.67 (q, J=4.5 Hz, 1H), 3.99 (s, 3H), 2.82 (d, 3H). $^{13}$C NMR (101 MHz, DMSO) δ 156.00, 150.93, 138.41, 136.21, 135.45, 128.22, 127.96, 127.65, 127.33, 127.11, 126.79, 126.12, 124.43, 123.42, 122.35, 121.53, 117.59, 110.33, 108.13, 56.16, 30.18. MS (ESI-TOF) for $C_{18}H_{15}F_3N_4O_3$ [M+H]$^+$ calculated 393.33, found 393.10.

Compound 29

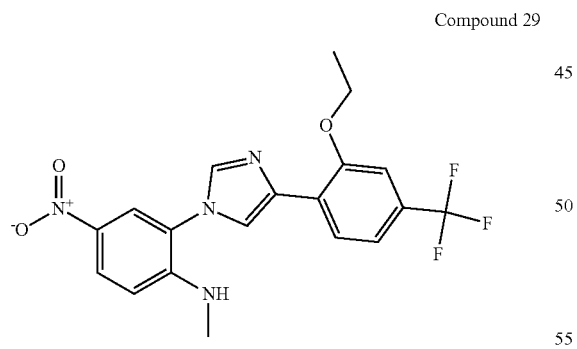

2-(4-(2-ethoxy-4-(trifluoromethyl)phenyl)-1H-imidazol-1-yl)-N-methyl-4-nitroaniline Yellow solid (95 mg, 82%). m.p. 208.8-209.8° C. $^1$H NMR (400 MHz, DMSO) δ 8.39 (d, J=8.0 Hz, 1H), 8.23 (dd, J=9.3, 2.6 Hz, 1H), 8.00 (dd, J=9.9, 1.8 Hz, 2H), 7.81 (d, J=0.8 Hz, 1H), 7.39 (d, J=8.2 Hz, 1H), 7.33 (s, 1H), 6.88 (d, J=9.4 Hz, 1H), 6.68 (d, J=4.8 Hz, 1H), 4.27 (q, 2H), 2.83 (d, 3H), 1.42 (t, J=6.9 Hz, 3H). $^{13}$C NMR (101 MHz, DMSO) δ 155.19, 150.77, 138.43, 136.35, 135.54, 127.55, 127.05, 126.78, 124.19, 121.83, 121.54, 117.53, 110.44, 108.86, 64.59, 30.19, 14.88. MS (ESI-TOF) for $C_{19}H_{17}F_3N_4O_3$ [M+H]$^+$ calculated 407.36, found 407.65.

Compound 30

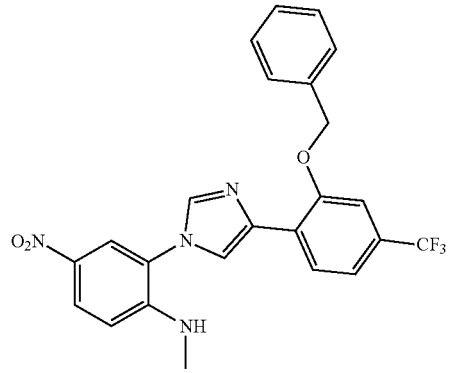

2-(4-(2-(benzyloxy)-4-(trifluoromethyl)phenyl)-1H-imidazol-1-yl)-N-methyl-4-nitroaniline Yellow solid (159 mg, 92%). m.p. 217.3-218.4° C. $^1$H NMR (400 MHz, DMSO) δ 8.40 (d, J=8.0 Hz, 1H), 8.21 (dd, J=9.3, 2.6 Hz, 1H), 7.99 (dd, J=16.5, 2.0 Hz, 2H), 7.77 (d, J=1.1 Hz, 1H), 7.54 (d, J=6.9 Hz, 2H), 7.46 (s, 1H), 7.41 (d, J=8.1 Hz, 1H), 7.39-7.24 (m, 3H), 6.85 (d, J=9.4 Hz, 1H), 6.72 (d, J=4.8 Hz, 1H), 5.39 (s, 2H), 2.82 (d, 3H). $^{13}$C NMR (101 MHz, DMSO) δ 154.90, 150.48, 138.34, 136.92, 136.26, 135.50, 128.85, 128.50, 128.30, 127.53, 127.12, 126.97, 123.84, 122.05, 121.46, 117.91, 110.38, 109.72, 70.53, 30.24. MS (ESI-TOF) for $C_{24}H_{19}F_3N_4O_3$ [M+H]$^+$ calculated 467.43, found 467.52.

Compound 31

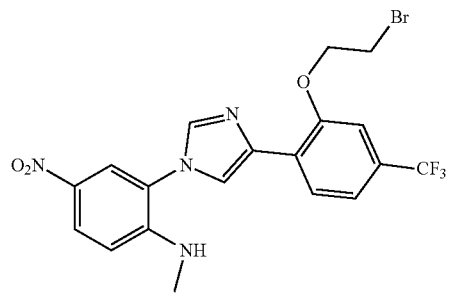

2-(4-(2-(2-bromoethoxy)-4-(trifluoromethyl)phenyl)-1H-imidazol-1-yl)-N-methyl-4-nitroaniline Yellow solid (109 mg, 90%). m.p. 209.3-210.5° C. $^1$H NMR (400 MHz, DMSO) δ 8.40 (d, J=8.0 Hz, 1H), 8.22 (d, J=9.2 Hz, 1H), 8.07 (s, 1H), 8.03 (s, 2H), 7.49-7.31 (m, 2H), 6.88 (d, J=9.2 Hz, 1H), 6.74 (d, J=3.5 Hz, 1H), 4.58 (s, 2H), 3.98 (s, 2H), 2.83 (d, 3H). $^{13}$C NMR (101 MHz, DMSO) δ 154.55, 150.50, 138.34, 135.99, 135.50, 128.00, 127.59, 126.95, 126.02, 123.88, 123.32, 122.51, 121.56, 118.13, 110.42, 109.20, 68.99, 32.13, 30.22. MS (ESI-TOF) for $C_{19}H_6BrF_3N_4O_3$ [M+H]$^+$ calculated 486.25, found 486.28.

Compound 32

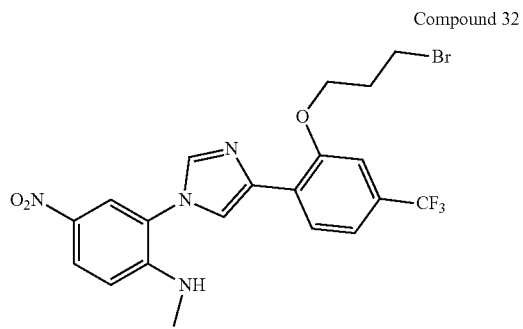 [SMILES: CNc1ccc([N+](=O)[O-])cc1-n1cnc(-c2ccc(C(F)(F)F)cc2OCCCBr)c1]

2-(4-(2-(3-bromopropoxy)-4-(trifluoromethyl)phenyl)-1H-imidazol-1-yl)-N-methyl-4-nitroaniline Yellow solid (153 mg, 90%). m.p. 213.3-214.8° C. $^1$H NMR (400 MHz, DMSO) δ 8.39 (d, J=7.8 Hz, 1H), 8.23 (d, J=9.1 Hz, 1H), 8.02 (s, 2H), 7.82 (s, 1H), 7.41 (d, J=13.2 Hz, 2H), 6.87 (d, J=9.2 Hz, 1H), 6.73 (s, 1H), 4.34 (s, 2H), 3.70 (d, 2H), 2.83 (d, 3H), 2.45-2.21 (m, 2H). $^{13}$C NMR (101 MHz, DMSO) δ 154.99, 150.76, 138.48, 136.19, 135.57, 127.79, 127.75, 124.13, 121.95, 121.61, 117.92, 117.88, 110.47, 109.05, 66.90, 40.61, 40.41, 40.20, 39.99, 39.78, 39.57, 39.36, 32.09, 31.83, 30.28. MS (ESI-TOF) for $C_2H_{18}BrF_3N_4O_3$ [M+H]$^+$ calculated 500.28, found 500.99.

Compound 33

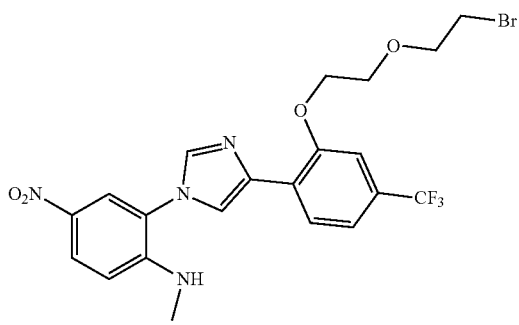

2-(4-(2-(3-bromopropoxy)-4-(trifluoromethyl)phenyl)-1H-imidazol-1-yl)-N-methyl-4-nitro aniline Yellow solid (178 mg, 92%). m. p. 188.1-189.9° C. $^1$H NMR (400 MHz, DMSO) δ 8.38 (d, J=8.0 Hz, 1H), 8.23 (dd, J=9.3, 2.5 Hz, 1H), 8.06-7.92 (m, 3H), 7.46-7.31 (m, 2H), 6.86 (d, J=9.4 Hz, 1H), 6.67 (d, J=4.7 Hz, 1H), 4.39-4.25 (m, 2H), 3.92-3.81 (m, 2H), 3.73 (t, 2H), 3.42 (t, 2H), 2.82 (d, 3H). $^{13}$C NMR (101 MHz, DMSO) δ 155.16, 150.95, 138.46, 136.31, 135.53, 127.47, 127.16, 126.14, 124.36, 123.44, 122.53, 121.62, 117.85, 110.44, 109.14, 70.64, 68.94, 67.99, 32.11, 30.26. MS (ESI-TOF) for $C_{21}H_2BrF_3N_4O_4$ [M+H]$^+$ calculated 530.31, found 530.11.

Compound 34

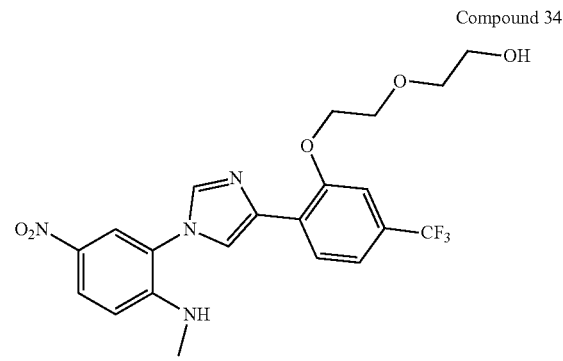 [SMILES: CNc1ccc([N+](=O)[O-])cc1-n1cnc(-c2ccc(C(F)(F)F)cc2OCCOCCO)c1]

2-(2-(2-(1-(2-(methylamino)-5-nitrophenyl)-1H-imidazol-4-yl)-5-(trifluoromethyl)phenoxy)ethoxy)ethanol Yellow solid (141 mg, 76%). m.p. 172.5-173.6° C. $^1$H NMR (400 MHz, DMSO) δ 8.37 (d, J=7.9 Hz, 1H), 8.23 (dd, J=9.2, 2.2 Hz, 1H), 7.99 (t, J=4.3 Hz, 3H), 7.40 (d, J=10.8 Hz, 2H), 6.87 (d, J=9.3 Hz, 1H), 6.68 (d, J=4.7 Hz, 1H), 4.46 (t, 1H), 4.33 (d, 2H), 3.84 (d, 2H), 3.42 (t, 2H), 3.32 (s, 2H), 2.83 (d, 3H). $^{13}$C NMR (101 MHz, DMSO) δ 155.18, 150.69, 138.32, 136.30, 135.50, 127.35, 124.03, 122.49, 121.57, 117.79, 110.38, 72.66, 69.24, 68.08, 60.49, 30.19. MS (ESI-TOF) for $C_{21}H_{21}F_3N_4O_5$ [M+H]$^+$ calculated 465.41, found 466.56.

Compound 35

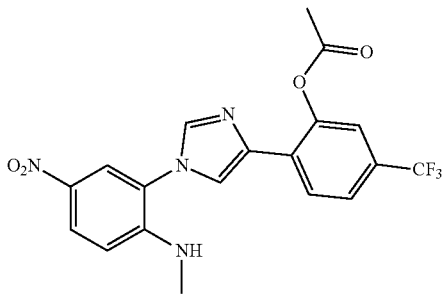

(1-(2-(methylamino)-5-nitrophenyl)-1H-imidazol-4-yl)-5-(trifluoromethyl)phenyl acetate Yellow solid (178 mg, 92%). m.p. 134.7-136.1° C. $^1$H NMR (400 MHz, DMSO) δ 8.34 (d, J=8.2 Hz, 1H), 8.23 (dd, J=9.3, 2.6 Hz, 1H), 8.03 (d, J=2.7 Hz, 2H), 7.83 (s, 1H), 7.75-7.62 (m, 2H), 6.88 (d, J=9.3 Hz, 1H), 6.73 (d, J=4.7 Hz, 1H), 2.82 (d, 3H), 2.38 (s, 3H). $^{13}$C NMR (101 MHz, DMSO) δ 169.42, 150.75, 146.94, 139.09, 135.54, 130.99, 128.81, 127.07, 124.32, 122.96, 121.41, 110.43, 30.17, 21.71. MS (ESI-TOF) for $C_{19}H_{15}F_3N_4O_4$ [M+H]$^+$ calculated 421.34, found 421.34.

Compound 36

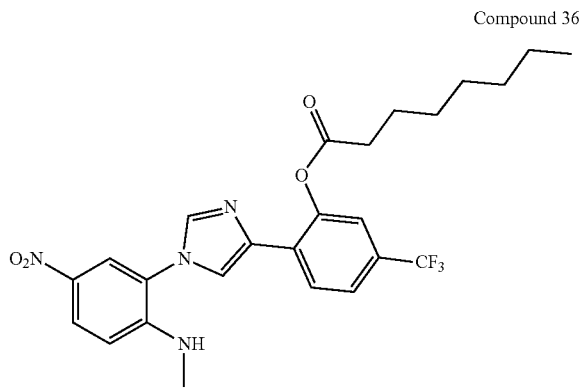 [SMILES: CCCCCCCC(=O)Oc1cc(C(F)(F)F)ccc1-c1cn(-c2cc([N+](=O)[O-])ccc2NC)cn1]

2-(1-(2-(methylamino)-5-nitrophenyl)-1H-imidazol-4-yl)-5-(trifluoromethyl)phenyl octanoate Yellow solid (105 mg, 91%). m.p. 150.6-152.2° C. $^1$H NMR (400 MHz, DMSO) δ 8.34 (d, J=8.2 Hz, 1H), 8.23 (dd, J=9.3, 2.4 Hz, 1H), 8.05-7.95 (m, 2H), 7.77 (s, 1H), 7.70 (d, J=8.3 Hz, 1H), 7.62 (s, 1H), 6.87 (d, J=9.3 Hz, 1H), 6.74 (d, J=4.7 Hz, 1H), 2.82 (d, 3H), 2.71 (t, 2H), 1.70-1.55 (m, 2H), 1.26 (ddd, 8H), 0.82 (t, 3H). $^{13}$C NMR (101 MHz, DMSO) δ 171.95, 150.68, 146.97, 139.05, 135.86, 135.52, 131.04, 128.81, 127.85, 127.53, 127.06, 125.60, 124.17, 122.99, 121.38, 110.44, 34.06, 31.41, 30.14, 28.73, 24.40, 22.40, 14.22. MS (ESI-TOF) for $C_{25}H_{27}F_3N_4O_4$ [M+H]$^+$ calculated 505.50, found 505.48.

Compound 37

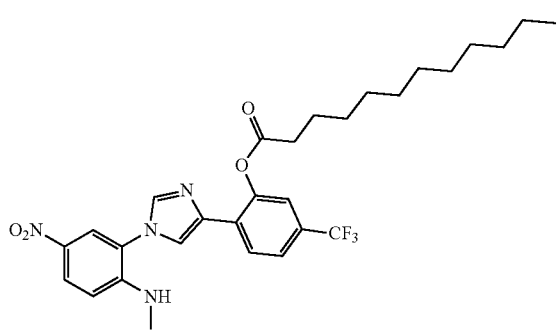

2-(1-(2-(methylamino)-5-nitrophenyl)-1H-imidazol-4-yl)-5-(trifluoromethyl)phenyl dodecanoate Yellow solid (154 mg, 90%). m.p. 158.3-159.6° C. H NMR (400 MHz, DMSO) δ 8.34 (d, J=8.2 Hz, 1H), 8.21 (dd, J=9.2, 2.1 Hz, 1H), 8.05-7.94 (m, 2H), 7.76 (s, 1H), 7.69 (d, J=8.3 Hz, 1H), 7.61 (s, 1H), 6.87 (d, J=9.3 Hz, 1H), 6.75 (d, J=4.6 Hz, 1H), 2.81 (d, 3H), 2.70 (t, 2H), 1.69-1.54 (m, 2H), 1.27-1.12 (m, 17H), 0.84 (t, 4H). $^{13}$C NMR (101 MHz, DMSO) δ 171.91, 150.66, 146.96, 139.02, 135.86, 135.51, 131.02, 128.81, 127.85, 127.53, 127.03, 125.59, 124.13, 123.01, 121.35, 121.31, 121.09, 110.42, 34.05, 31.69, 30.12, 29.37, 29.17, 29.11, 29.04, 28.78, 24.38, 22.49, 14.28. MS (ESI-TOF) for $C_{29}H_{35}F_3N_4O_4$ [M+H]$^+$ calculated 561.61, found 561.83.

Compound 38

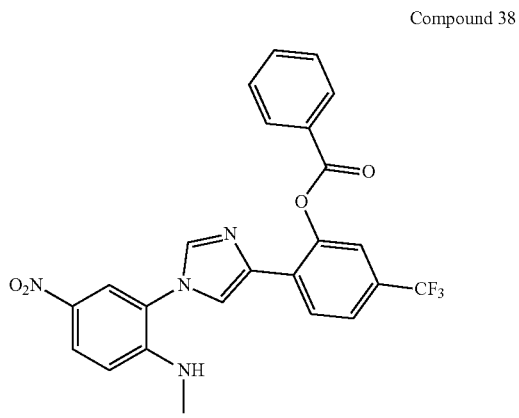 [SMILES: CNc1ccc([N+](=O)[O-])cc1-n1cnc(-c2ccc(C(F)(F)F)cc2OC(=O)c2ccccc2)c1]

2-(1-(2-(methylamino)-5-nitrophenyl)-1H-imidazol-4-yl)-5-(trifluoromethyl)phenyl benzoate Yellow solid (186 mg, 90%). m.p. 203.3-204.3° C. $^1$H NMR (400 MHz, DMSO) δ 8.37 (d, J=8.3 Hz, 1H), 8.22 (t, J=7.9 Hz, 2H), 8.14 (d, J=9.2 Hz, 1H), 8.00 (d, J=9.3 Hz, 1H), 7.89-7.80 (m, 2H), 7.75 (dd, J=18.0, 8.6 Hz, 2H), 7.65 (d, J=9.1 Hz, 1H), 7.60 (t, J=7.8 Hz, 2H), 6.77 (d, J=9.3 Hz, 1H), 6.62 (s, 1H), 2.65 (d, 3H). $^{13}$C NMR (101 MHz, DMSO) δ 164.63, 150.23, 147.06, 139.06, 135.91, 135.46, 134.55, 131.23, 130.37, 129.39, 129.26, 128.99, 126.95, 123.73, 121.15, 110.40, 30.04. MS (ESI-TOF) for $C_{24}H_{17}F_3N_4O_4$ [M+H]$^+$ calculated 483.41, found 483.25.

Compound 39

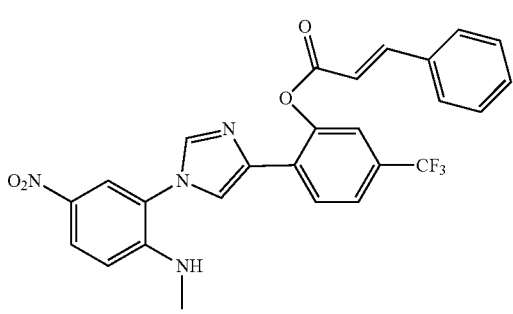

(1-(2-(methylamino)-5-nitrophenyl)-1H-imidazol-4-yl)-5-(trifluoromethyl)phenyl cinnamate Yellow solid (119 mg, 85%). m.p. 209.3-210.2° C. H NMR (400 MHz, DMSO) δ 8.40 (d, J=8.1 Hz, 1H), 8.16 (d, J=9.2 Hz, 1H), 8.03 (s, 1H), 7.98 (s, 1H), 7.93 (d, J=16.0 Hz, 1H), 7.85 (s, 1H), 7.82-7.68 (m, 4H), 7.44 (d, J=6.8 Hz, 3H), 7.07 (d, J=16.0 Hz, 1H), 6.77 (d, J=9.3 Hz, 1H), 6.67 (d, J=4.6 Hz, 1H), 2.67 (d, 3H). C NMR (101 MHz, DMSO) δ 164.92, 150.52, 147.46, 146.88, 139.11, 135.80, 135.50, 134.27, 131.35, 131.15, 129.31, 129.09, 128.82, 127.90, 127.58, 127.01, 124.04, 123.18, 121.52, 121.30, 117.65, 110.38, 30.07. MS (ESI-TOF) for $C_{26}H_{19}F_3N_4O_4$ [M+H]$^+$ calculated 509.45, found 509.38.

Compound 40

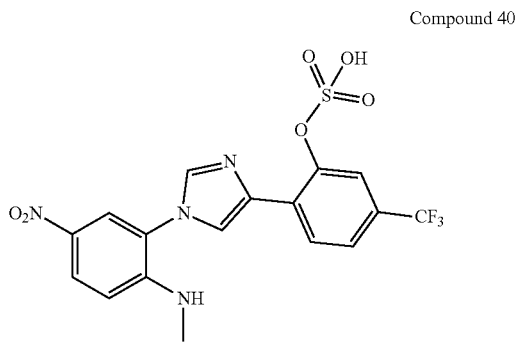 [SMILES: CNc1ccc([N+](=O)[O-])cc1-n1cnc(-c2ccc(C(F)(F)F)cc2OS(=O)(=O)O)c1]

(1-(2-(methylamino)-5-nitrophenyl)-1H-imidazol-4-yl)-5-(trifluoromethyl)phenyl disulfate Yellow solid (186 mg, 90%). m.p. 173.3-175.6° C. $^1$H NMR (400 MHz, DMSO) δ 8.36 (d, J=8.2 Hz, 1H), 8.24 (dd, J=9.3, 2.6 Hz, 1H), 8.08-7.95 (m, 2H), 7.89 (d, J=20.3 Hz, 2H), 7.49 (d, J=7.8 Hz, 1H), 6.88 (d, J=9.4 Hz, 1H), 6.65 (d, J=4.8 Hz, 1H), 2.83 (d, 3H). $^{13}$C NMR (101 MHz, DMSO) δ 150.73, 150.19, 138.37, 136.28, 135.51, 129.33, 127.44, 127.18, 124.09, 122.23, 121.41, 119.86, 117.08, 110.50, 30.20. MS (ESI-TOF) for $C_7H_3F_3N_4O_6S$ [M+H]$^-$ calculated 455.37, found 455.30.

Compound 42

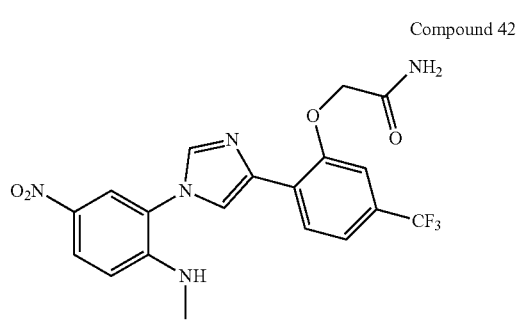 [SMILES: CNc1ccc([N+](=O)[O-])cc1-n1cnc(-c2ccc(C(F)(F)F)cc2OCC(N)=O)c1]

(2-(1-(2-(methylamino)-5-nitrophenyl)-1H-imidazo-4-yl)-5-(trifluoromethyl)phenoxy)acetamide Yellow solid (52 mg, 92%). m.p. 226.7-228.9° C. $^1$H NMR (400 MHz, DMSO) δ 8.37 (d, J=8.0 Hz, 1H), 8.24 (dd, J=9.3, 2.6 Hz, 1H), 8.19 (s, 1H), 8.05-7.96 (m, 2H), 7.59 (s, 1H), 7.43 (d, 0.1=8.2 Hz, 1H), 7.35 (s, 1H), 7.24 (s, 1H), 6.88 (d, J=9.4 Hz, 1H), 6.68 (d, J=4.7 Hz, 1H), 4.74 (s, 2H), 2.83 (d, 3H). $^{13}$C NMR (101 MHz, DMSO) δ 169.81, 154.54, 150.78, 138.40, 136.24, 135.52, 127.69, 127.13, 124.20, 123.00, 121.61, 110.44, 99.98, 67.58, 30.26. MS (ESI-TOF) for $C_9H_6F_3N_5O_4$ [M+H]$^+$ calculated 436.36, found 436.57.

Compound 41

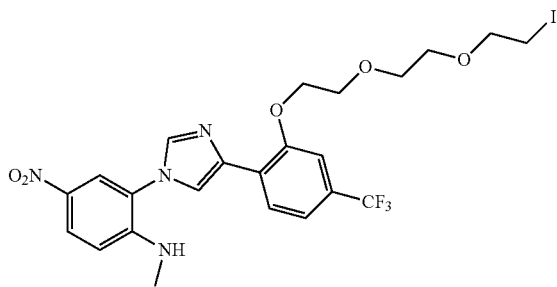

2-(4-(2-(2-(2-(2-iodoethoxy)ethoxy)ethoxy)-4-(trifluoromethyl)phenyl)-1H-imidazole-1-yl)-N-methyl-4-nitroaniline Yellow solid (81 mg, 84%). m.p. 166.7-168.2° C. $^1$H NMR (400 MHz, CDCl3) δ 8.33 (d, J=7.0 Hz, 2H), 8.16 (d, J=2.4 Hz, 1H), 7.97 (s, 1H), 7.82 (s, 1H), 7.34 (d, J=7.9 Hz, 1H), 7.17 (s, 1H), 6.81 (d, J=9.3 Hz, 1H), 5.19 (s, 1H), 4.39-4.24 (m, 2H), 4.03-3.88 (m, 2H), 3.72-3.62 (m, 2H), 3.58 (t, 2H), 3.55-3.47 (m, 2H), 3.13 (t, 2H), 3.01 (d, 3H). $^{13}$C NMR (101 MHz, CDCl3) δ 154.82, 149.79, 136.90, 136.53, 127.34, 127.01, 125.43, 123.71, 121.49, 109.50, 71.72, 70.16, 69.48, 67.31, 30.02, 2.66. MS (ESI-TOF) for $C_{23}H_4F_3IN_4O_5$ [M+H]$^+$ calculated 621.36, found 620.81.

Compound 43

2-(4-(3-(2-aminoethoxy)-4-(trifluoromethyl)phenyl)-1H-imidazol-1-yl)-N-methyl-4-nitroaniline Yellow solid (39 mg, 80%). m.p. 136.9-139.5° C. $^1$H NMR (400 MHz, DMSO) δ 8.37 (d, J=8.0 Hz, 1H), 8.24 (dd, J=9.3, 2.5 Hz, 1H), 8.04 (d, J=2.6 Hz, 1H), 8.01 (s, 1H), 7.96 (s, 1H), 7.49-7.39 (m, 2H), 6.89 (d, J=9.4 Hz, 1H), 6.63 (d, J=4.4 Hz, 1H), 4.37 (t, 2H), 3.28 (d, 4H), 2.83 (d, 3H). $^{13}$C NMR NMR (101 MHz, DMSO) δ 154.97, 150.74, 138.40, 136.16, 135.52, 127.91, 127.76, 127.22, 127.01, 126.03, 124.16, 123.33, 122.28, 121.59, 118.05, 110.44, 109.44, 68.90, 30.21. MS (ESI-TOF) for $C_{19}H_{18}F_3N_5O_3$ [M+H]$^+$ calculated 422.37, found 422.02.

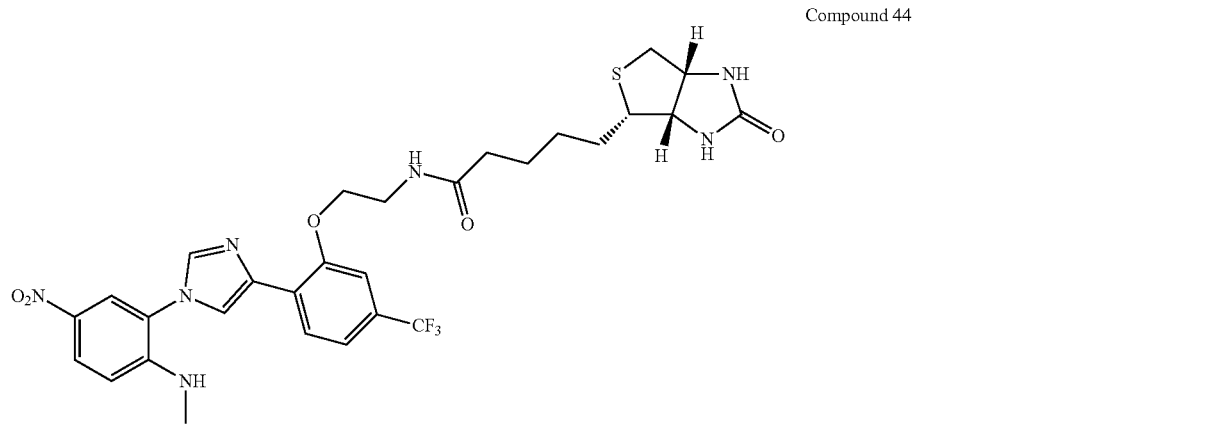 [SMILES: CNc1ccc([N+](=O)[O-])cc1-n1cnc(-c2ccc(C(F)(F)F)cc2OCCNC(=O)CCCC[C@@H]2SC[C@@H]3NC(=O)N[C@@H]32)c1]

Compound 44

N-(2-(2-(1-(2-(methylamino)-5-nitrophenyl)-1H-imidazol-4-yl)-5-(trifluoromethyl)phenoxyl)ethyl)-5-((3AS,4S,6AR)-2-oxohexahydro-1H-thieno[3,4-d]imidazol-4-yl)pentanamide Yellow solid (42.76 mg, 93%). m.p. 118.7-120.5° C. $^1$H NMR (400 MHz, CDCl$_3$) δ 8.34-8.19 (m, 2H), 8.12 (d, J=2.4 Hz, 1H), 7.74 (d, 0.1=25.4 Hz, 2H), 7.33 (d, J=8.2 Hz, 1H), 7.14 (dd, J=13.3, 8.0 Hz, 2H), 6.76 (d, J=9.3 Hz, 1H), 6.31 (s, 1H), 5.28 (d, J=4.3 Hz, 1H), 5.12 (s, 1H), 4.35-4.27 (m, 1H), 4.24 (t, 2H), 4.13-4.04 (m, 1H), 3.75 (d, 2H), 2.98 (d, 4H), 2.78 (dd, 1H), 2.54 (d, 1H), 2.11 (t, 2H), 1.50 (d, 4H), 1.28 (d, 3H). $^{13}$C NMR (101 MHz, DMSO) δ 172.71, 163.12, 155.07, 150.90, 138.36, 136.06, 135.44, 127.57, 124.42, 121.62, 117.76, 110.33, 108.93, 79.62, 67.67, 61.40, 59.59, 55.82, 53.74, 42.03, 38.31, 35.56, 31.37, 30.22, 28.55, 25.41, 22.47, 14.36, 12.75. MS (ESI-TOF) for C$_{29}$H$_{32}$F$_3$N$_7$O$_5$S [M+H]$^+$ calculated 648.67, found 647.57.

Ethyl 2-(2-(1-(2-(methylamino)-5-nitrophenyl)-1H-imidazol-4-yl)-5-(trifluoromethyl)phenoxy)-5-((3aS, 4S, 6aR)-2-oxohexahydro-1H-thieno[3,4-d]imidazol-4-yl)pentanoate Yellow solid (67 mg, 71%). m.p. 79.1-80.5° C. $^1$H NMR (400 MHz, CDCl$_3$) δ 8.34-8.24 (m, 2H), 8.12 (d, J=2.5 Hz, 1H), 7.78 (s, 1H), 7.71 (s, 1H), 7.35 (d, J=8.0 Hz, 1H), 7.10 (s, 1H), 6.79 (d, J=9.3 Hz, 1H), 5.88 (s, 1H), 5.51 (d, 1H), 5.26 (s, 1H), 4.54 (d, 2H), 4.47-4.37 (m, 1H), 4.30 (t, 2H), 4.24-4.15 (m, 1H), 3.00 (t, 4H), 2.84 (dd, 1H), 2.65 (d, 1H), 2.20 (t, 2H), 2.03 (s, 2H), 1.52-1.42 (m, 3H), 1.28 (d, 3H). $^{13}$C NMR (101 MHz, CDCl$_3$) δ 173.17, 154.50, 150.05, 137.01, 136.62, 127.45, 127.15, 123.89, 121.58, 121.18, 118.06, 109.65, 108.12, 66.49, 61.96, 59.95, 55.37, 40.42, 33.60, 29.95, 28.13, 24.55. MS (ESI-TOF) for C$_{29}$H$_{31}$F$_3$N$_6$O$_6$S [M+H]$^+$ calculated 649.65, found 649.68.

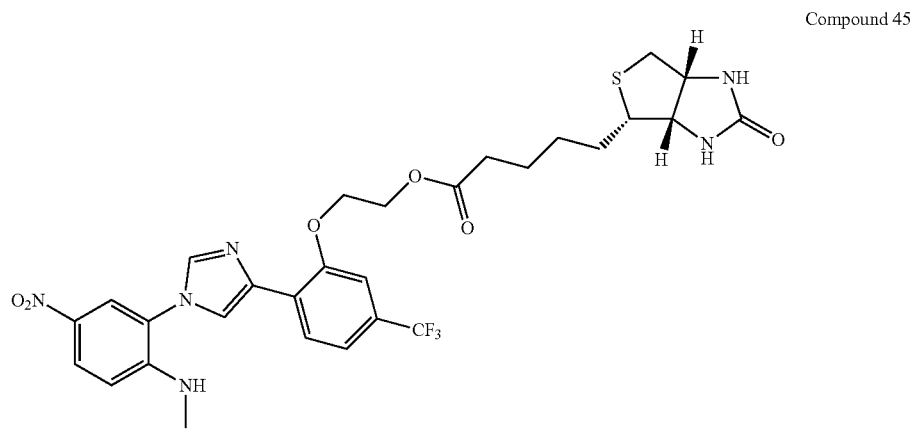 [SMILES: CNc1ccc([N+](=O)[O-])cc1-n1cnc(-c2ccc(C(F)(F)F)cc2OCCOC(=O)CCCC[C@@H]2SC[C@@H]3NC(=O)N[C@@H]32)c1]

Compound 45

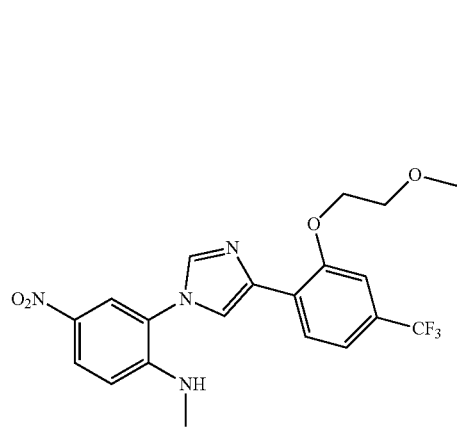

Compound 46

Ethyl ((3aS, 4S, 6aR)-2-(2-(2-(2-(2-(methylamino)-5-nitrophenyl)-1H-imidazol-4-yl)-5-(Trifluoromethyl)phenoxy)ethoxy)yl)-2-oxohexahydro-1H-thieno[3,4-d]imidazol-4-yl)pentanoate Yellow solid (85 mg, 63%). m.p. 53.2-54.7° C. $^1$H NMR (400 MHz, CDCl$_3$) δ 8.26 (dd, J=9.2, 2.4 Hz, 1H), 8.17 (d, J=7.9 Hz, 1H), 8.10 (d, J=2.5 Hz, 1H), 7.88 (s, 1H), 7.73 (s, 1H), 7.32 (d, J=8.2 Hz, 1H), 7.07 (s, 1H), 6.79 (d, J=9.4 Hz, 1H), 6.08 (d, J=48.6 Hz, 3H), 5.76 (s, 1H), 4.49 (t, 2H), 4.30 (s, 1H), 4.25-4.16 (m, 3H), 4.07 (s, 2H), 3.89 (s, 2H), 3.68-3.60 (m, 2H), 3.10 (d, 2H), 3.01 (d, 3H), 2.86 (d, 3H), 2.17 (s, 2H), 1.66 (s, 3H), 1.53 (d, J=7.0 Hz, 4H). $^{13}$C NMR (101 MHz, CDCl$_3$) δ 173.38, 164.72, 154.68, 150.17, 137.18, 136.44, 127.13, 125.47, 123.82, 121.84, 121.23, 117.80, 109.74, 108.16, 71.64, 68.86, 67.12, 63.08, 62.12, 60.32, 55.55, 40.61, 33.57, 31.52, 30.01, 28.37, 24.51, 22.58, 14.05, 2.93. MS (ESI-TOF) for C$_{31}$H$_{35}$F$_3$N$_6$O$_7$S [M+H]$^+$ calculated 693.71, found 693.01.

129.20, 127.05, 125.59, 123.79, 122.74, 121.74, 121.34, 117.74, 109.47, 108.20, 70.28, 69.36, 68.94, 67.27, 63.07, 61.83, 60.02, 55.48, 40.42, 33.58, 29.87, 28.21, 24.58. MS (ESI-TOF) for C$_{33}$H$_{39}$F$_3$N$_6$O$_8$S [M+H]$^+$ calculated 737.76, found 738.86.

Example 16 Detection of TLR1/2 Activation Activity of Compound 22 and Other Compounds TLR1/2 activation activity was detected using TLR1/2 HEK BLUE cells. TLR1/2 HEK BLUE cells were cultured in DMEM medium containing 10% fetal bovine serum, 1% penicillin and streptomycin, and incubated in a 37° C. cell incubator containing 5% CO$_2$.

HEK BLUE TLR1/2 cells were spread in a 384-well plate at 20,000 cells/well, cultured at 37° C., 5% CO$_2$ for 24 hours, 25 μL per well. When the cells grew well, 100 μM compound and doubling-diluted for 11 concentration gradients. After the cells were kept for 24 hours in the CO$_2$

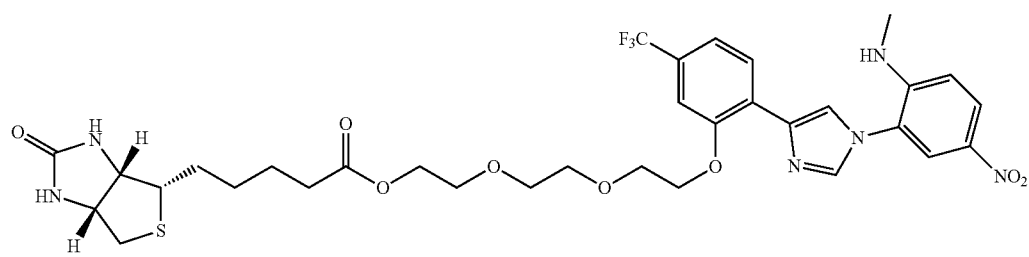

Compound 47

Ethyl 5-(2-(2-(2-(2-(methylamino)-5-nitrophenyl)-1H-imidazol-4-yl)-5-(trifluoromethyl)phenoxy Ethoxy)ethoxy)ethyl 5-(3AS,4S,6AR)-2-oxohexahydro-1H-thieno[3,4-d]imidazol-4-yl)pentanoate Yellow solid (22.6 mg, 75%). m.p. 73.1-74.4° C. $^1$H NMR (400 MHz, CDCl$_3$) δ 8.30 (dd, J=9.1, 2.7 Hz, 2H), 8.15 (d, J=2.6 Hz, 1H), 7.92 (d, J=1.2 Hz, 1H), 7.76 (d, J=0.9 Hz, 1H), 7.36 (d, J=7.5 Hz, 1H), 7.17 (s, 1H), 6.78 (d, J=9.3 Hz, 1H), 5.66 (s, 1H), 5.39 (d, 1H), 5.04 (s, 1H), 4.46 (dd, 1H), 4.34-4.27 (m, 2H), 4.25 (dd, 1H), 4.15-4.06 (m, 2H), 3.98-3.88 (m, 2H), 3.65 (dd, 2H), 3.51 (td, 4H), 3.10 (ddd, 1H), 2.98 (t, 3H), 2.88 (d, 1H), 2.71 (d, 1H), 2.28 (t, 2H), 1.68-1.53 (m, 4H), 1.45-1.30 (m, 2H). $^{13}$C NMR (101 MHz, CDCl$_3$) δ 173.52, 163.75, 154.76, 150.12, 137.29, 136.60, incubator, 40 μL of indigo blue solution was added to each well of the plate in the dark, and reading was conducted 4 times in an interval of 15 minutes at 620 nm to detect the signal intensity of SEAP in the cell supernatant.

As shown in FIG. 1, compound 22 can significantly activate the signal intensity of TLR1/2 alkaline phosphatase (SEAP), even at a low concentration (15 nM). See Table 7 for the results of other compounds.

The results show that this series of compounds have a good ability to activate TLR1/2 and have good development potential.

TABLE 7

| Compound No. | TLR1/2 activation activity EC$_{50}$ (nM) |
|---|---|
| 1 | >1000[‡] |
| 2 | >1000 |
| 3 | >1000[‡] |
| 4 | >1000[‡] |
| 5 | >1000 |
| 6 | NA[†] |
| 7 | NA[†] |
| 8 | NA[†] |
| 9 | >1000[‡] |
| 10 | NA[†] |
| 11 | >1000 |
| 12 | NA[†] |
| 13 | NA[†] |
| 14 | NA[†] |
| 15 | >1000 |
| 16 | NA[†] |
| 17 | NA[†] |
| 18 | >1000[‡] |
| 19 | NA[†] |
| 20 | NA[†] |
| 21 | 24.87 ± 6.15 |
| 22 | 4.88 ± 0.79 |
| 23 | 5.14 ± 0.07 |
| 24 | 432.86 ± 0.05 |
| 25 | 45.57 ± 3.15 |
| 26 | 192.19 ± 17.19 |
| 27 | >1000 |
| 28 | 92.26 ± 12.3 |
| 29 | >1000 |
| 30 | >1000 |
| 31 | >1000 |
| 32 | >1000 |
| 33 | >1000 |
| 34 | >1000 |
| 35 | 18.83 ± 3.65 |
| 36 | 56.32 ± 7.31 |
| 37 | 112.69 ± 12.69 |
| 38 | 16.85 ± 2.79 |
| 39 | 11.98 ± 2.67 |
| 40 | 49.13 ± 3.82 |
| 41 | >1000 |
| 42 | >1000 |
| 43 | >1000 |
| 44 | 764.48 ± 10.18 |
| 45 | >1000 |
| 46 | >1000 |
| 47 | >1000 |

[†]: Lack of activation effect with the highest concentration of 100 μM.
[‡]: The highest SEAP signal value is less than 50% of the activation value of compound 22.
NA: No activation.

What is claimed is:

1. A compound, or a pharmaceutically acceptable salt thereof, wherein the compound has a structural formula below: Compound 23

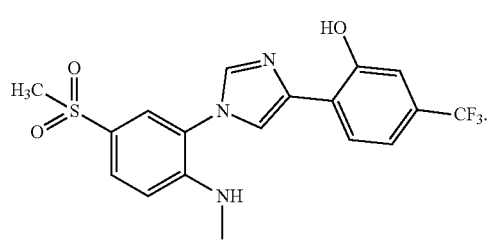

2. A preparation method of the compound according to claim 1, comprising the following steps:

1) allowing compound A1

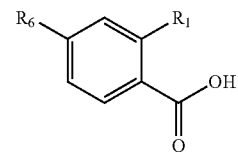

to react as catalyzed by inethyllithium to obtain compound A2

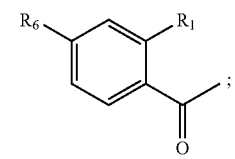

allowing the compound A2

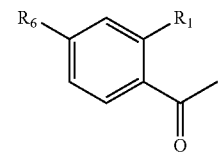

to react in a presence of tetrabutylammonium tribromide to obtain compound A3

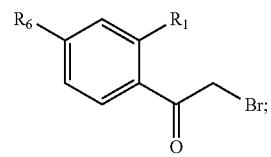

2) allowing compound B1

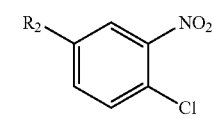

to react in methylamine to give an amino-substituted compound B2

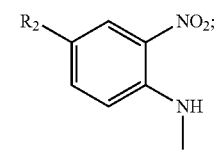

reducing the amino-substituted compound B2 to obtain compound B3

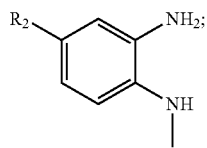

or aminomethylating compound B5

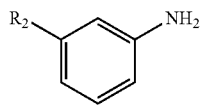

to obtain the compound B3;

3) reacting compound B3 with triethyl orthofomiate to form a ring to obtain compound B4

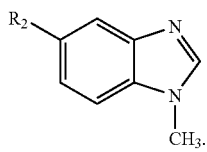

4) reacting the compound 134 with the compound A3 to obtain compound B6

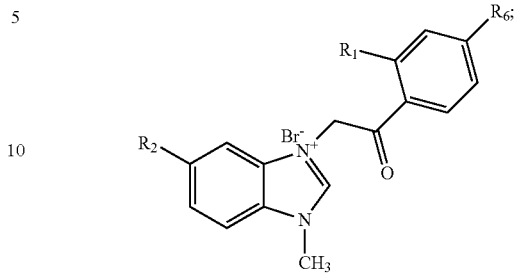

5) refluxing the compound B6 under acidic conditions to obtain the compound according to claim 1;

wherein $R_1$, $R_2$ and $R_6$ in the compounds A3, B1, B2, B3, B4 and B5 for preparing the compound according to claim 1 are as follows:

$R_1$=OH, $R_6$=CF$_3$, $R_2$=SO$_2$CH$_3$.

3. A pharmaceutical composition, comprising the compound according to claim 1, or a pharmaceutically acceptable salt thereof, and a pharmaceutically acceptable carrier or an excipient.

4. A method for regulating an activity activation level of URI and TLR2 alkaline phosphatases in vivo, comprising administering the compound according to claim 1 to a subject.

* * * * *